(12) United States Patent
Harrah et al.

(10) Patent No.: US 11,096,568 B2
(45) Date of Patent: Aug. 24, 2021

(54) ACCESS DEVICE METHODS OF USING THE SAME

(71) Applicants: Boston Scientific Scimed, Inc., Maple Grove, MN (US); Oxford University Innovation Limited, Oxford (GB)

(72) Inventors: Timothy P. Harrah, Cambridge, MA (US); Jerry Timothy Long, Jr., Jamaica Plain, MA (US); Jessica Williams, Thousand Oaks, CA (US); Benjamin Turney, Oxford (GB); Sarah Waters, Oxford (GB); Derek Moulton, Oxford (GB); Peter J. Pereira, Mendon, MA (US); Adam Perry Nodiff, Southborough, MA (US); Eric Wong, South Grafton, MA (US); Kimberly DeGraaf, Holden, MA (US); Mark Andrew Hera, Holden, MA (US); Daryl Christopher Donatelli, Brookline, MA (US); Niraj Prasad Rauniyar, Plymouth, MN (US); Melissa Graves, Brighton, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 15/946,389

(22) Filed: Apr. 5, 2018

(65) Prior Publication Data
US 2018/0289249 A1    Oct. 11, 2018

Related U.S. Application Data

(60) Provisional application No. 62/482,337, filed on Apr. 6, 2017, provisional application No. 62/552,819, filed on Aug. 31, 2017.

(51) Int. Cl.
*A61B 1/00* (2006.01)
*A61B 1/307* (2006.01)
(Continued)

(52) U.S. Cl.
CPC .......... *A61B 1/307* (2013.01); *A61B 1/00087* (2013.01); *A61B 1/00135* (2013.01);
(Continued)

(58) Field of Classification Search
CPC ....... A61B 1/12; A61B 1/307; A61B 1/00087; A61B 1/00131; A61B 1/00135;
(Continued)

(56) References Cited

U.S. PATENT DOCUMENTS

| | | |
|---|---|---|
| 5,213,093 A | 5/1993 | Swindle |
| 2006/0041186 A1 | 2/2006 | Vancaillie |

(Continued)

FOREIGN PATENT DOCUMENTS

| | | |
|---|---|---|
| CN | 101384223 A | 3/2009 |
| CN | 102159276 A | 8/2011 |

(Continued)

OTHER PUBLICATIONS

International Search Report and Written Opinion for PCT Application No. PCT/US2018/026566, dated Jun. 21, 2018, 15 pages.

(Continued)

*Primary Examiner* — Eduardo C Robert
*Assistant Examiner* — Christina Negrellirodriguez
(74) *Attorney, Agent, or Firm* — Brake Hughes Bellermann LLP

(57) ABSTRACT

According to an aspect, a medical device includes an elongate member having a sidewall. The sidewall defines a lumen. The lumen has a non-circular cross-sectional shape.

12 Claims, 24 Drawing Sheets

(51) Int. Cl.
    *A61B 1/015*     (2006.01)
    *A61B 1/12*     (2006.01)
    *A61B 1/018*     (2006.01)
    *A61B 1/32*     (2006.01)
    *G16H 40/63*     (2018.01)
    *A61B 17/34*     (2006.01)

(52) U.S. Cl.
    CPC .............. *A61B 1/015* (2013.01); *A61B 1/018* (2013.01); *A61B 1/12* (2013.01); *A61B 1/32* (2013.01); *A61B 2017/3433* (2013.01); *A61B 2017/3445* (2013.01); *A61B 2017/3449* (2013.01); *A61B 2217/007* (2013.01); *G16H 40/63* (2018.01)

(58) Field of Classification Search
    CPC ......... A61B 1/012; A61B 1/015; A61B 1/018; A61B 1/32
    See application file for complete search history.

(56) References Cited

U.S. PATENT DOCUMENTS

| | | |
|---|---|---|
| 2008/0091074 A1 | 4/2008 | Kumar et al. |
| 2012/0143006 A1* | 6/2012 | Avitsian ............. A61B 1/00094 600/121 |
| 2015/0087907 A1* | 3/2015 | Konstorum ........ A61B 1/00135 600/121 |

FOREIGN PATENT DOCUMENTS

| | | |
|---|---|---|
| CN | 105392416 A | 3/2016 |
| CN | 105491935 A | 4/2016 |
| JP | H10276980 A | 10/1998 |
| JP | 2000509305 A | 7/2000 |
| JP | 2016059710 A | 4/2016 |
| JP | 2016529033 A | 9/2016 |
| WO | 9740878 A1 | 11/1997 |

OTHER PUBLICATIONS

Office Action for Japanese Application No. 2019-549469, dated Sep. 23, 2020, 5 pages.

Office Action for Chinese Application No. 201880014556.2 (with English Translation), dated May 7, 2021, 22 pages.

* cited by examiner

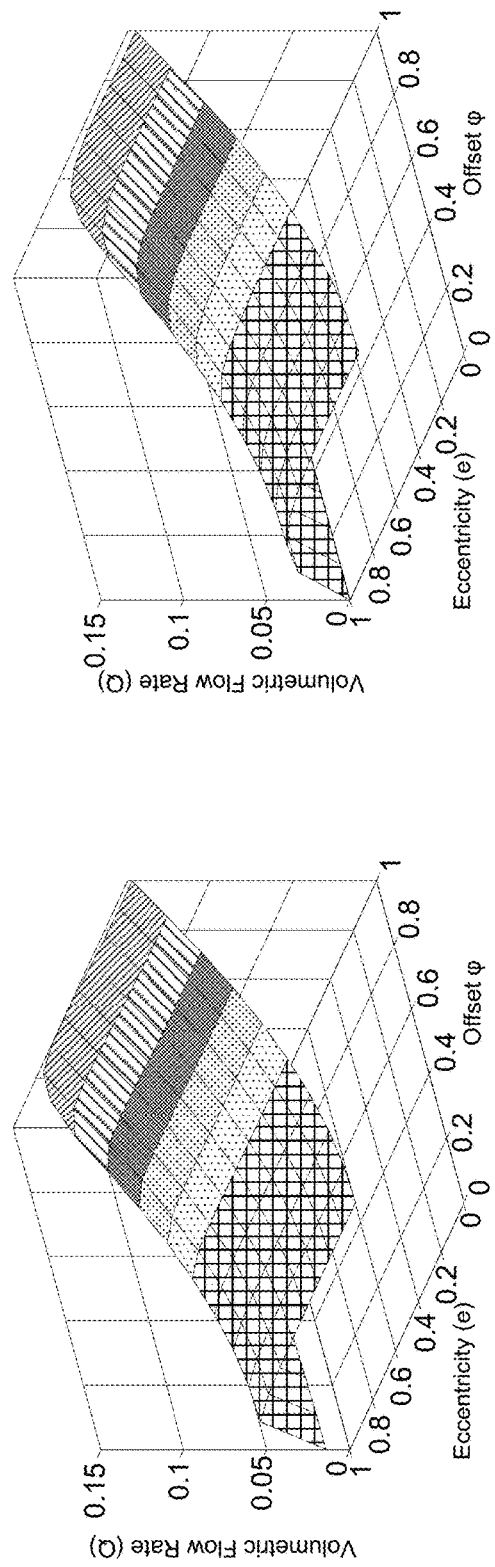
FIG. 30B
FIG. 30A
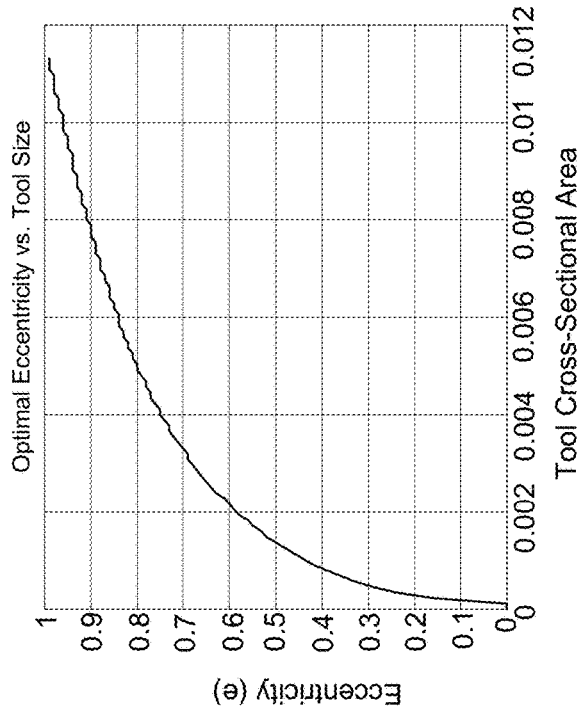
FIG. 31

ACCESS DEVICE METHODS OF USING THE SAME

CROSS-REFERENCE TO RELATED APPLICATIONS

This application is a Nonprovisional of, and claims priority to, U.S. Provisional Patent Application No. 62/482,337 filed on Apr. 6, 2017, entitled "Modeling of Scope Irrigation and Related Systems and Methods" and U.S. Provisional Patent Application No. 62/552,819, filed on Aug. 31, 2017, entitled "Access Device and Methods of Using the Same", both of which are incorporated by reference herein in their entirety.

TECHNICAL FIELD

This disclosure relates generally to medical devices and more particularly to medical devices such as access devices or sheaths that include improved fluid dynamics. This disclosure also relates generally to modelling and related systems and methods. More specifically, the disclosure relates to modelling of scope irrigation and related systems and methods.

BACKGROUND

A variety of medical procedures are performed using an access device or an access sheath. For example, access devices or access sheaths may be used in procedures such as kidney stone treatment procedures (nephrolithiasis).

In some procedures that use access devices or access sheaths, it may be necessary or advantageous for the physician to visualize or see the procedure. Improved visibility may facilitate or make the procedure easier for the physician to perform. In some procedures, visibility may be improved by increasing the amount of fluid (volume) and increasing the pressure of the fluid (flow rate). However, in some cases high internal, intrarenal pressure, may case adverse side effects. For example, high intrarenal pressure may cause an increased risk of post treatment complications such as pyelovenous backflow and subsequent sepsis.

Accordingly, is may be desirable to provide a device, such as an access device or access sheath that allows for visibility during a medical procedure. It may also be desirable to provide a device, such as an access device or access sheath that improves visibility and/or optimizes fluid flow and limits or reduces the internal pressure such as the intrarenal pressure.

SUMMARY

According to an aspect, a medical device includes an elongate member having a sidewall. The sidewall defines a lumen. The lumen has a non-circular cross-sectional shape. In some embodiments, the medical device may be a scope such as a scope used during a ureteroscopy procedure.

In some embodiments, the lumen has a first diameter having a first size and a second diameter of a second size, the first size being different than the second size, the first diameter being disposed substantially perpendicular to the second diameter.

In some embodiments, the lumen has a first diameter having a first size and a second diameter of a second size, the first size being different than the second size, the first diameter being disposed substantially perpendicular to and intersecting the second diameter.

In some embodiments, the sidewall includes an inner surface and an outer surface, the inner surface defining the lumen, the outer surface being disposed opposite the inner surface.

In some embodiments, the sidewall includes an inner surface and an outer surface, the inner surface defining the lumen, the outer surface being disposed opposite the inner surface, a positioning member being disposed on the inner surface of the sidewall.

In some embodiments, the sidewall includes an inner surface and an outer surface, the inner surface defining the lumen, the outer surface being disposed opposite the inner surface, a positioning member being disposed on the inner surface of the sidewall, the positioning member extending along the inner surface of the sidewall parallel to a longitudinal axis of the elongate member.

In some embodiments, the sidewall includes an inner surface and an outer surface, the inner surface defining the lumen, the outer surface being disposed opposite the inner surface, a positioning member being disposed on the inner surface of the sidewall, the positioning member extending along the inner surface of the sidewall from a first end portion of the sidewall to a second end portion of the sidewall.

In some embodiments, the sidewall includes an inner surface and an outer surface, the inner surface defining the lumen, the outer surface being disposed opposite the inner surface, a positioning member being disposed on the inner surface of the sidewall, the positioning member being configured to help retain a medical instrument within lumen.

In some embodiments, the sidewall includes an inner surface and an outer surface, the inner surface defining the lumen, the outer surface being disposed opposite the inner surface, a positioning member being disposed on the inner surface of the sidewall, the positioning member being configured to help retain a medical instrument along a first side portion of the lumen.

In some embodiments, the sidewall includes a first positioning member and a second positioning member, the first positioning member being disposed within the lumen defined by the sidewall, the second positioning member being disposed within the lumen, the second positioning member being spaced from and disposed distally of the first positioning member.

In some embodiments, the sidewall includes a first positioning member and a second positioning member, the first positioning member being disposed within the lumen defined by the sidewall, the second positioning member being disposed within the lumen, the second positioning member being spaced from and disposed adjacent the first positioning member.

In some embodiments, the device includes a side port defining a lumen, the lumen of the side port being in fluid communication with the lumen defined by the sidewall.

In some embodiments, the device includes a side port defining a lumen, the lumen of the side port being in fluid communication with the lumen defined by the sidewall, the side port including a valve disposed within the lumen defined by the side port, the valve being configured to regulate flow of material within the lumen defined by the side port.

In some embodiments, the device includes a side port defining a lumen, the lumen of the side port being in fluid communication with the lumen defined by the sidewall, and a collection member coupled to the side port, the collection member being configured to collect material that passes through the lumen defined by the side port.

In some embodiments, the device includes a handle member coupled to the elongate member.

According to another aspect, a medical device includes an elongate member having a sidewall, the sidewall defining a lumen, the lumen having a non-circular cross-sectional shape, the sidewall including an inner surface and an outer surface, the inner surface defines the lumen, the outer surface being disposed opposite the inner surface, a positioning member being disposed on the inner surface of the sidewall, the positioning member being configured to help retain a medical instrument within lumen; a side port defining a lumen, the lumen of the side port being in fluid communication with the lumen defined by the sidewall, the side port including a valve disposed within the lune defined by the side port, the valve being configured to regulate flow of material within the lumen defined by the side port; and a collection member coupled to the side port, the collection member being configured to collect material that passes through the lumen defined by the side port.

In some embodiments, the device includes a handle member coupled to the elongate member.

According to another aspect, a method of using a medical device includes inserting the medical device into a body of a patient, the medical device including an elongate member having a lumen, the lumen having a non-circular cross-section; and inserting a medical instrument into the lumen defined by the medical device.

In some embodiments, the inserting the medical instrument includes inserting the medical instrument into or through the lumen defined by the medical device such that the medical instrument is disposed along one side of the lumen.

In some embodiments, the medical device includes a positioning member disposed within the lumen defined by the medical device, the inserting the medical instrument includes inserting the medical instrument into the lumen defined by the medical device such that at least a portion of the medical instrument is disposed between the positioning member and an inner surface of the sidewall.

BRIEF DESCRIPTION OF THE DRAWINGS

FIGS. 30A and 30B illustrate volumetric flow rate as a function of e and $\varphi$ for $\theta_e=0$.

FIG. 31 illustrates the maximum eccentricity value predicted for $\varphi=0.99$ and $\theta_e=0$, as the cross-sectional area of the tool increases.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
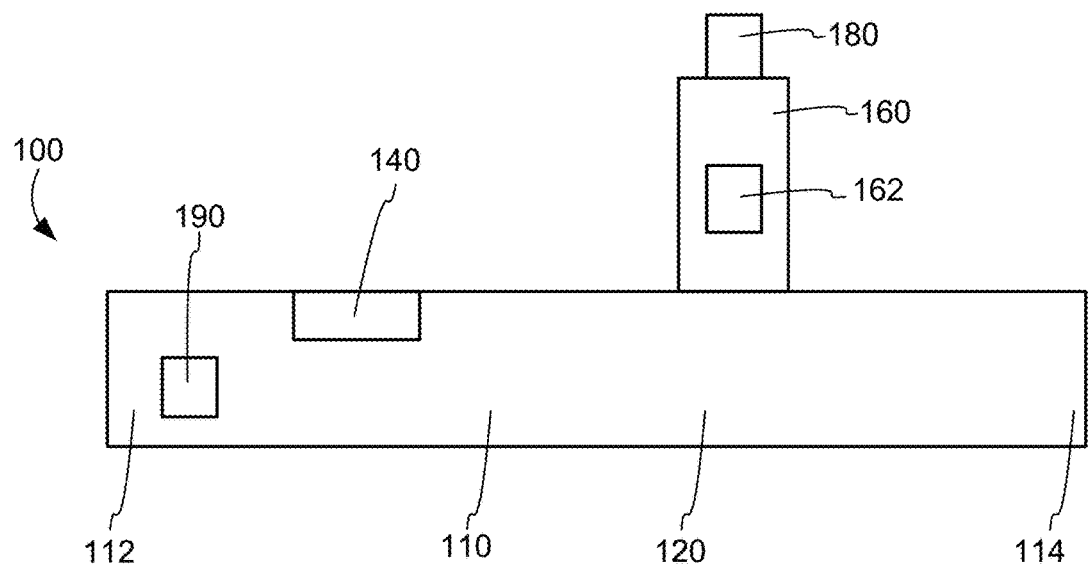
FIG. 1 is a schematic illustration of a medical device according to an embodiment.

FIG. 1 is a schematic illustration of a medical device 100 according to an embodiment of the invention. The medical device 100 may be used in surgical procedures. For example, in some embodiments the medical device 100 may be placed within a body of a patient to create an access or port for further medical procedures. More specifically, in some embodiments, the medical device 100 may be placed within the body of the patient such that a distal end portion of the medical device 100 is disposed within the body of the patient and a proximal end portion of the medical device 100 extends from the body of the patient. In some embodiments, an additional or secondary medical device or a medical instrument may be inserted into the body of the patient via the medical device 100 to perform an additional medical procedure.

In the illustrated embodiment, the medical device 100 includes an elongate member 110. The elongate member 110 includes a first or proximal end portion 112 and a second or distal end portion 114. The elongate member defines a lumen that extends from the first or proximal end portion 112 to the second or distal end portion 114. In some embodiments, the elongate member 110 includes a sidewall 120. In some such embodiments, the sidewall 120 defines the lumen.

In some embodiments, the elongate member 110 is linear or substantially straight or linear. In other embodiments, the elongate member 110 is curved or is flexible and may form a curve or have a curved portion. In some embodiments, the elongate member 110 or the sidewall 120 may have a non-circular cross-sectional shape. For example, the elongate member 110 or the sidewall 120 may have an oval or oblong cross-sectional shape. In some such embodiments, flow of fluid within the lumen may be increased or optimized.

In other embodiments, the elongate member 110 or the sidewall 120 may have a round or circular cross-sectional shape. In yet other embodiments, the elongate member 110 or the sidewall 120 has a different cross-sectional shape, such as square, rectangular, triangular, or any other shape.

The medical device 100 also includes a positioning member 140. The positioning member 140 is configured to help retain a secondary medical device or another medical instrument within the lumen. For example, in some embodiments, the positioning member 140 is configured to help retain the secondary medical device or medical instrument in position within the lumen. Specifically, the positioning member 140 may be configured to help retain the secondary medical device or medical instrument along one side or along one portion of the lumen of the device 100. In some such embodiments, fluid may flow along or within the portion of the lumen that is not occupied by the secondary medical device or medical instrument.

In some embodiments, the positioning member 140 is disposed within the lumen. For example, in some embodiments, the positioning member 140 is coupled to an inner surface of the sidewall 120. In some embodiments, the positioning member 140 is coupled to the elongate member 110 or the sidewall 120 via an adhesive or other coupling mechanism. In other embodiments, the positioning member 140 is integrally formed with the elongate member 110 or the sidewall 120.

As will be described in more detail below, in some embodiments, the positioning member 140 extends along a longitudinal axis of the elongate member 110 or the sidewall 120. In some embodiments, the positioning member 140 extends from the first or proximal end portion 112 to the second or distal end portion 114. In some embodiments, the medical device 100 includes more than one positioning member. For example, in some embodiments, the medical device 100 may include a first positioning member disposed at a proximal end portion of the elongate member and a second positioning member disposed at a mid-portion or at the distal end portion of the elongate member. In another embodiment, the medical device 100 includes a first positioning member disposed at the proximal end portion of the elongate member and second positioning member disposed adjacent the first positioning member at the proximal end portion of the elongate member. In yet other embodiments, the medical device 100 includes more than two positioning members.

In the illustrated embodiment, the medical device 100 includes a side port 160. The side port 160 defines a lumen. The side port 160 is coupled to the elongate member 110 or the sidewall 120 such that the lumen of the side port 160 is in fluid communication with the lumen defined by the elongate member 110 or the sidewall 120. The side port 160 is configured to pass fluid into and receive fluid from the lumen defined by the elongate member 110 or the sidewall 120.

In the illustrated embodiment, the side port 160 includes a valve 162. The valve 162 is disposed within the lumen defined by the side port 160. The valve 162 is configured to help regulate or control the fluid flow through the lumen defined by the side port 160. In some embodiments, the valve 162 is a stop cock or stop valve. In other embodiments, the valve 162 is a different type of valve.

In the illustrated embodiment, the medical device 100 includes a collection member 180. The collection member 180 is coupled to the side port 160. The collection member 180 is configured to collect material that is disposed within the fluid that flows through or within the lumen of the side port 160. For example, the collection member 180 may be a filter that is configured to collect kidney stones or kidney stone fragments that pass from the body of the patient and through the lumen of the side port 160.

In the illustrated embodiment, the medical device 100 includes a handle member or handle portion 190. The handle member or handle portion 190 is coupled to the elongate member 110 or the sidewall 120. The handle member or handle portion 190 is configured to be grasped by a physician or other medical practitioner to place the medical device 100 within a body of a patient or during the use of the medical device 100.

In use, the medical device 100 may be inserted into a body of a patient. In some embodiments, the medical device 100 may be inserted into the body of the patient such that the second or distal end portion 114 of the elongate member 110 is disposed within the body of the patient and the first or proximal end portion 112 of the elongate member 110 is disposed outside of the body of the patient (or extends from the body of the patient). For example, in some embodiments, the medical device 100 may be placed within the body of the patient such that the second or distal end portion 114 is disposed within a kidney or a ureter of the patient. In other embodiments, the medical device 100 is placed within the body of the patient such that the second or distal end portion 114 is disposed at a different location with the body of the patient.

Once the medical device 100 is disposed within the body of the patient, other medical devices or medical instruments may be inserted into the body of the patient though the lumen defined by the elongate member 110. For example, in some embodiments, the other medical device or medical instrument may be inserted into the lumen defined by the elongate member 110 or the sidewall 120 such that the other medical device or medical instrument is disposed along one side of the lumen. Accordingly, such other or secondary medical devices may be used to perform additional medical procedures once such device is disposed within the body of the patient. In some embodiments, the other medical device or medical instrument is a scope. In other embodiments, the medical instrument is another type of medical device.

Figure 2:
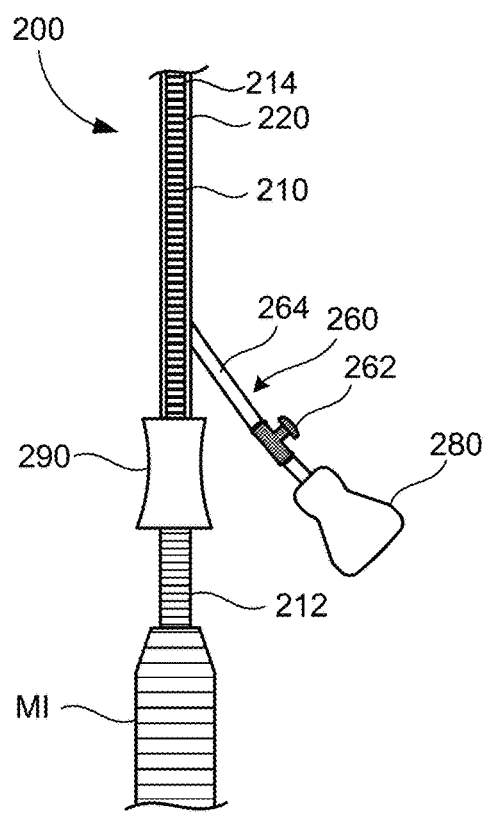
FIG. 2 is a top view of a medical device according to an embodiment.
Figure 3:
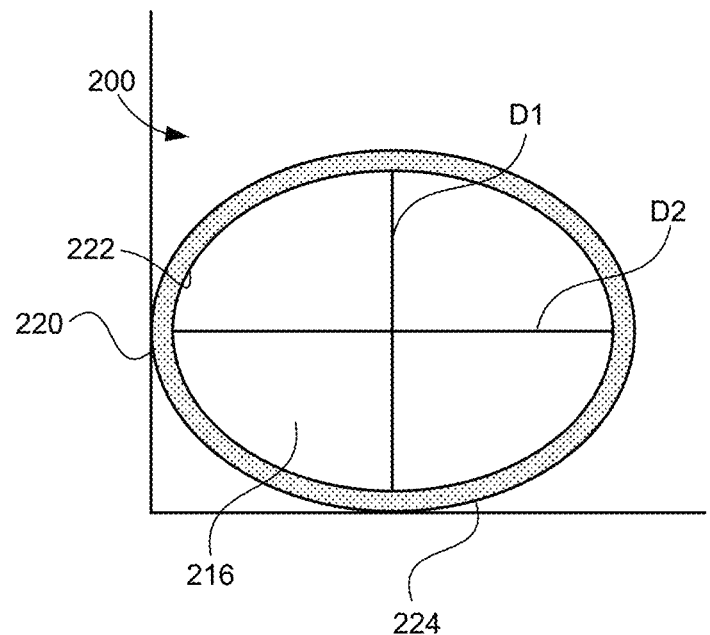
FIGS. 3-5 are cross-sectional views of the medical device of FIG. 2.
Figure 4:
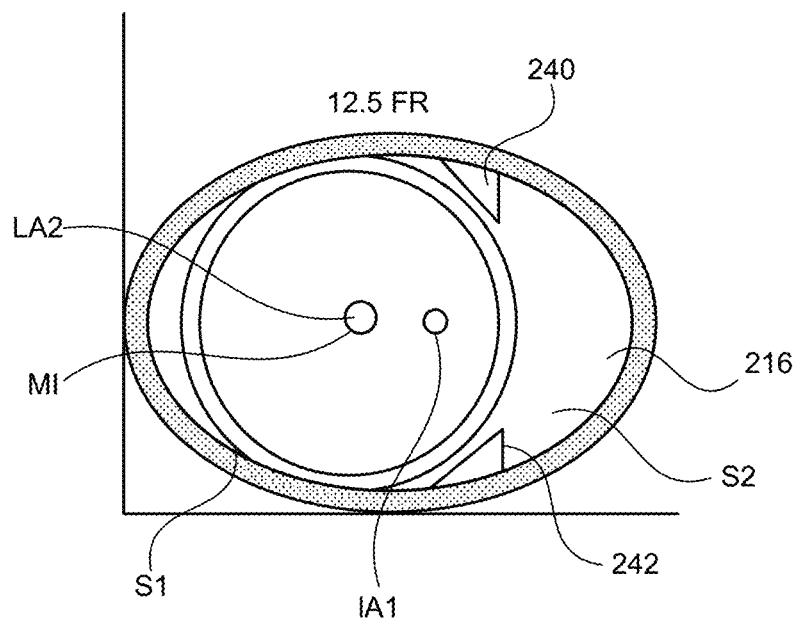
Figure 5:
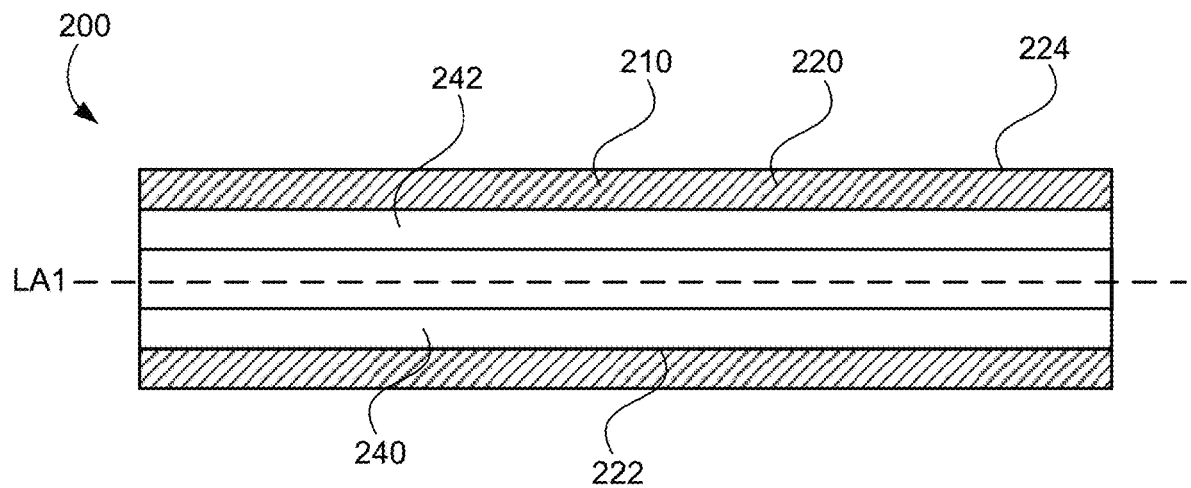

FIG. 2 is a top view of a medical device 200 according to an embodiment. FIGS. 3-5 are cross-sectional views of the medical device 200.

The medical device 200 may be used in surgical procedures. For example, in some embodiments the medical device 200 may be placed within a body of a patient to create an access or port for further medical procedures. More specifically, in some embodiments, the medical device 200 may be placed within the body of the patient such that a distal end portion of the medical device 200 is disposed within the body of the patient and a proximal end portion of the medical device 200 extends from the body of the patient. In some embodiments, an additional or secondary medical device or a medical instrument may be inserted into the body of the patient via the medical device 200 to perform an additional medical procedure.

In the illustrated embodiment, the medical device 200 includes an elongate member 210. The elongate member 210 includes a first or proximal end portion 212 and a second or distal end portion 214. The elongate member defines a lumen 216 that extends from the first or proximal end portion 212 to the second or distal end portion 214.

In the illustrated embodiment, the elongate member 210 includes a sidewall 220. The sidewall 220 includes an inner surface 222 and an outer surface 224. The inner surface 222 is disposed opposite the outer surface 224. The inner surface 222 defines the lumen 216.

In some embodiments, the elongate member 210 is linear or substantially straight or linear. In other embodiments, the elongate member 210 is curved or is flexible and may form a curve or have a curved portion.

In the illustrated embodiment, the elongate member 210 or the sidewall 220 may have a non-circular cross-sectional shape. The elongate member 210 or the sidewall 220 has an oval or oblong cross-sectional shape. Specifically, as best illustrated in FIG. 3, the elongate member 210 or the sidewall 220 has inner diameters of different sizes. Diameter D1 is of a first size and diameter D2 is of a second size different than the first size. In the illustrated embodiment, diameter D1 is disposed perpendicular or substantially perpendicular to diameter D2. In other embodiments, the diameters are not disposed perpendicularly to each other. In the illustrated embodiment, flow of fluid within the lumen 216 may be increased or optimized. In some embodiments, the size difference between D1 and D2 is about 0.33 mm. For example, in some embodiments, the size difference between D1 and D2 is between 0.25 mm and 0.08 mm. In other embodiments, the size difference between D1 and D2 is less than 0.25 mm. In yet other embodiments, the size difference between D1 and D2 is greater than 0.5 mm. In some embodiments, the diameter in the vertical direction is about 0.34 cm and the diameter in the horizontal direction is about 0.39 cm. In other embodiments, the diameter in the vertical direction is between 0.30 cm and 0.40 cm and the diameter in the horizontal direction is between 0.35 cm and 0.45 cm.

In other embodiments, the elongate member or the sidewall may have a round or circular cross-sectional shape. In yet other embodiments, the elongate member or the sidewall has a different cross-sectional shape, such as square, rectangular, triangular, or any other shape.

The medical device 200 also includes a positioning member 240. The positioning member 240 is configured to help retain a secondary medical device or another medical instrument within the lumen. For example, in some embodiments, the positioning member 240 is configured to help retain the secondary medical device or medical instrument in position within the lumen. In the illustrated embodiment, the medical device also includes a second positioning member 241. The second positioning member 241 is structurally and functionally similar to the positioning member 240. Accordingly, only positioning member 240 will be discussed in detail.

As best illustrated in FIG. 4, the positioning member 240 is configured to help retain the secondary medical device or medical instrument MI along one side S1 or along one portion of the lumen 216. In some such embodiments, fluid may flow along or within a second side S2, the portion of the lumen 216 that is not occupied by the secondary medical device or medical instrument MI. Specifically, when the secondary medical device MI is disposed within the lumen 216, the secondary medical device MI and the medical device 200 are not disposed in a coaxial relationship. In other words, the longitudinal axis LA2 of the secondary medical device MI is offset from the longitudinal axis LA1 of the elongate member 210 or sidewall 220.

In the illustrated embodiment, the positioning member 240 is disposed within the lumen 216. For example, the positioning member 240 may be coupled to the inner surface 222 of the sidewall 220. In some embodiments, the positioning member 240 is coupled to the elongate member 210 or the sidewall 220 via an adhesive or other coupling mechanism. In other embodiments, the positioning member 240 is integrally formed with the elongate member 210 or the sidewall 220.

As best illustrated in FIG. 5, in the illustrated embodiment, the positioning member 240 extends along a longitudinal axis LA1 of the elongate member 210 or the sidewall 220. The positioning member 240 extends from the first or proximal end portion 212 to the second or distal end portion 214.

Figure 6:
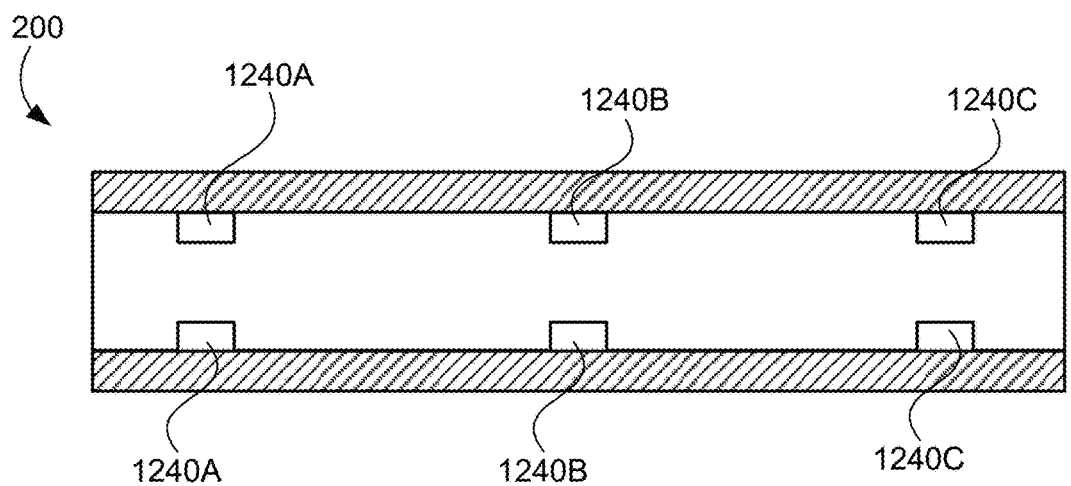
FIG. 6 is a cross-sectional view of a medical device according to an embodiment.

As illustrated FIG. 6, in another embodiment, positioning members 1240A, 1240B, and 1240C are disposed at different locations along the elongate member or the sidewall. In the illustrated embodiment, a couple of the positioning members 1240A are disposed at or near a proximal end portion of the elongate member or sidewall. These positioning members 1240A are disposed adjacent to each other. Specifically, these positioning members 1240A are disposed at the same longitudinal location along the longitudinal axis of the elongate member or sidewall, but are spaced circumferentially from each other.

Positioning members 1240B are disposed at a mid-section of the elongate member or sidewall. Positioning members 1240C are disposed at a distal end portion of the elongate member or sidewall.

In the illustrated embodiment, the medical device 200 includes a side port 260. The side port 260 defines a lumen 264. The side port 260 is coupled to the elongate member 210 or the sidewall 220 such that the lumen 264 of the side port 260 is in fluid communication with the lumen 216 defined by the elongate member 210 or the sidewall 220. The side port 260 is configured to pass fluid into and receive fluid from the lumen 216 defined by the elongate member 210 or the sidewall 220.

In some embodiments, a fluid source or a fluid vacuum may be coupled to the side port 260 to facilitate the passing of fluid into the lumen 216 and the receiving of fluid from the lumen 216.

In the illustrated embodiment, the side port 260 includes a valve 262. The valve 262 is disposed within the lumen 264 defined by the side port 260. The valve 262 is configured to help regulate or control the fluid flow through the lumen 264 defined by the side port 260. In the illustrated embodiment, the valve 262 is a stop cock or stop valve. In other embodiments, the valve 262 is a different type of valve.

In the illustrated embodiment, the medical device 200 includes a collection member 280. The collection member 280 is coupled to the side port 260. The collection member 280 is configured to collect material that is disposed within the fluid that flows through or within the lumen 264 of the side port 260. For example, the collection member 280 may be a filter that is configured to collect kidney stones or kidney stone fragments that pass from the body of the patient and through the lumen 264 of the side port 260.

In the illustrated embodiment, the medical device 200 includes a handle member or handle portion 290. The handle member or handle portion 290 is coupled to the elongate member 210 or the sidewall 220. The handle member or handle portion 290 is configured to be grasped by a physician or other medical practitioner to place the medical device 200 within a body of a patient or during the use of the medical device 200.

In use, the medical device 200 may be inserted into a body of a patient. In some embodiments, the medical device 200 may be inserted into the body of the patient such that the second or distal end portion 214 of the elongate member 210 is disposed within the body of the patient and the first or proximal end portion 212 of the elongate member 210 is disposed outside of the body of the patient (or extends from the body of the patient). For example, in some embodiments, the medical device 200 may be placed within the body of the patient such that the second or distal end portion 214 is disposed within a kidney or ureter of the patient. In other embodiments, the medical device 200 is placed within the body of the patient such that the second or distal end portion 214 is disposed at a different location with the body of the patient.

Once the medical device 200 is disposed within the body of the patient, other medical devices or medical instruments may be inserted into the body of the patient though the lumen defined by the elongate member 210. For example, in some embodiments, the other medical device or medical instrument may be inserted into the lumen defined by the elongate member 210 or the sidewall 220 such that the other medical device or medical instrument is disposed along one side of the lumen. Accordingly, such other or secondary medical devices may be used to perform additional medical procedures once such device is disposed within the body of the patient. In some embodiments, the other medical device or medical instrument is a scope. In other embodiments, the medical instrument is another type of medical device.

Figure 7:
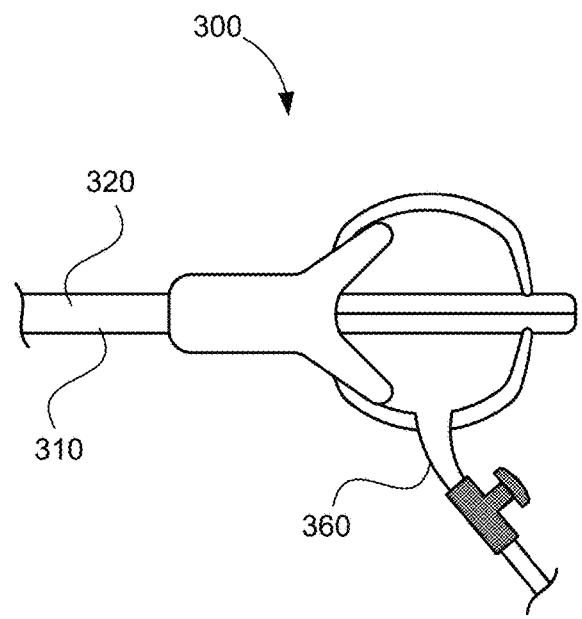
FIG. 7 is a top view of a medical device according to an embodiment.

FIG. 7 is a top view of a portion of a medical device 300 according to another embodiment. In this embodiment, the side port 360 is coupled to the elongate member 310 or the sidewall 320 at or near a proximal end portion of the elongate member 310 or the sidewall 320.

Figure 8:
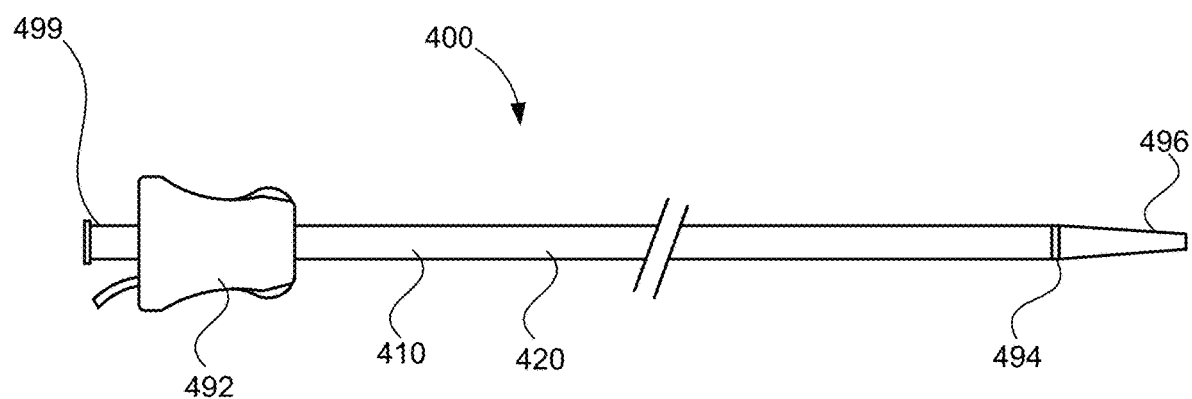
FIG. 8 is a top view of a medical device according to an embodiment.

FIG. 8 is a top view of a medical device 400 according to another embodiment. Similar to the above embodiments, the medical device 400 includes an elongate member 410 or a sidewall 420 that has a non-circular cross-section. The medical device 400 also includes a positioning member or positioning members that are disposed within the lumen defined by the elongate member 410 or the sidewall 420.

In the illustrated embodiment, the medical device 400 also includes a hub 492. The hub 492 is configured to engage the secondary medical device or medical instrument that is inserted into the lumen defined by the elongate member 410 or the sidewall 420. The hub 492 may be configured to engage the secondary medical device or medical instrument such that the secondary medical device or medical instrument is removably coupled to the hub 492. In some embodiments, the hub 492 may include a latch or a latch system that is configured to engage the secondary medical device or medical instrument to removably coupled the secondary medical device or medical instrument to the hub 492.

In the illustrated embodiment, the elongate member 410 or sidewall 420 may be configured to be resistant to kinking. For example, in some embodiments, the elongate member 410 or sidewall 420 may include a sheath that is reinforced with a coil, such as a stainless steel coil. Additionally, in some embodiments, the outer surface of the elongate member 410 or sidewall may include a coating such as a hydrophilic coating. The coating may be configured to facilitate the insertion or placement of the device within the body of the patient.

In the illustrated embodiment, the medical device 400 includes a radiopaque marker 494. The radiopaque marker 494 is may be viewed via fluoroscopy to confirm the placement of the device 400 within the body of the patient.

In the illustrated embodiment, the medical device 400 includes a tapered tip portion 496. In some embodiments, the tapered tip portion 496 may be stiffer or more rigid than other portions of the elongate member 410. For example, the tapered tip portion 496 may be formed of a material that is of a different durometer than the material that forms the remainder of the elongate member 410. In some embodiments, the tapered tip is configured to facilitate placement of the device 400 within the body of the patient. Additionally, the tapered tip may reduce trauma to the patient during the insertion of the device into the body of the patient.

In some embodiments, an inner obturator 499 may be used to facilitate the placement or insertion of the device into the body of the patient. For example, in some embodiments, the inner obturator 499 is a tubular member that may be inserted into the lumen of the device 400 and used to provide support to the device during the placement of the device 400. Once the device 400 is placed within the body, the inner obturator 499 may be removed from the device 400 and the body of the patient. In some embodiment, the inner obturator 499 has a circular cross-section. In other embodiments, the inner obturator 499 has a cross-section of a different shape.

Figure 9:
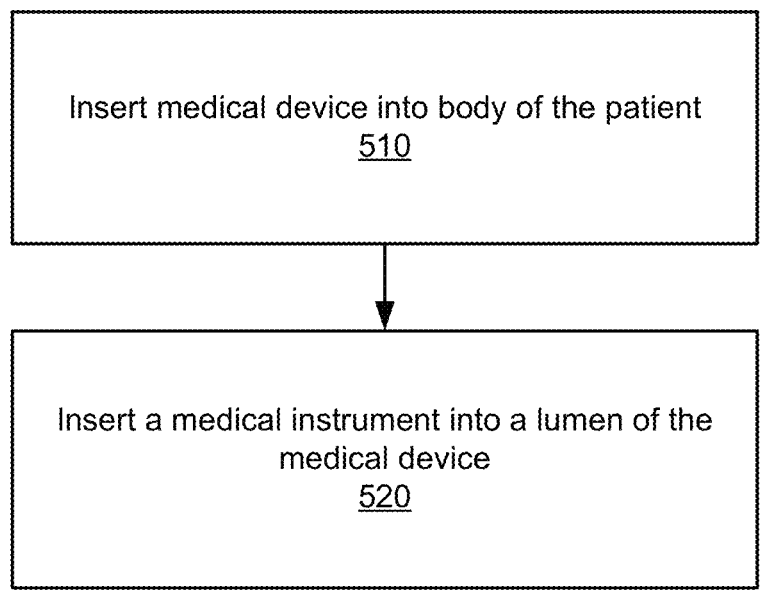
FIG. 9 is a flow chart of a method according to an embodiment.

FIG. 9 is a flow chart of a method 500 according to an embodiment of the invention. At 510, a medical device is inserted into a body of the patient. In some embodiments, the medical device is inserted into the body of the patient such that a distal end portion is disposed within the body and a proximal end portion of the device is disposed outside of the body of the patient. For example, in some embodiments, the device may be placed within the body of the patient such that the distal end portion is disposed within a kidney or ureter of the patient.

At 520, a secondary medical device or medical instrument is inserted into the body of the patient via a lumen defined by the medical device. In some embodiments, the secondary medical device or medical instrument is inserted into the lumen such that the secondary medical device or medical instrument is disposed at or along one side portion of the lumen. In some embodiments, the secondary medical device or medical instrument is a scope. In other embodiments, it is a device for another type of medical procedure.

In some embodiments, ureteroscopy may be performed to diagnose and treat urinary tract diseases and ureteral strictures. In some procedures, ureteroscopy is a surgical procedure for removing kidney stones. In some ureteroscopy procedures, irrigation or continuous irrigation is used to clear the field-of-view of the operator and to open up the ureter. Accordingly, it can be beneficial to optimize irrigation for visualization. Some challenges include loss of irrigation when tools are inserted into the patient, high kidney pressures, retropulsion of stones, and difficulties controlling and maintaining flow rates.

In some cases, mathematical modeling can be used to determine the impact of parameters (such as scope size and shape, tool size and shape, and irrigation set-up) on irrigation flow, validate mathematical models with experiments, and used models to optimize irrigation. The modeling can be used to analyze the flow effect of a straight or linear scope, a deflected scope, and using the scope with a working or secondary tool (such as effect of position and cross-sectional shape).

A medical device as described herein, such as a ureteroscope, may be inserted retrograde through the urinary tract such that diagnosis and treatment of urinary tract abnormalities may be performed. As described herein, an exemplary medical device or ureteroscope may have a handle coupled to a shaft.

The handle may have any shape suitable for gripping and controlling the ureteroscope. A proximal end of the shaft is coupled to a distal end of the handle. The ureteroscope may include a steering mechanism for deflecting a distal end of the shaft along one or more planes. The shaft includes at least one working channel extending between its proximal and distal ends. In some examples, the shaft may include one or more electronic components, such as a camera or other imaging device, a light source, and/or other sensor. Additionally or alternatively, the shaft may include a lumen for light delivery and/or steering control members.

The handle also may include an umbilicus hub or connector for facilitating electrical connections and functions, such as transferring data and/or powering a light source. In addition, the handle may include at least one port (e.g., a T-shaped or Y-shaped luer port connection). The port may be fluidly coupled to one or more sources of irrigation and/or suction fluid. Accordingly, irrigation fluid may be delivered (e.g., pumped) through the working channel via the port, and out of the distal end of the shaft, to aid in visualization and/or open up a ureter. The port also may receive an insertion portion (e.g., a shaft) of a secondary medical device, to allow entry of the secondary medical device into the working channel of the shaft. A distal end of the medical device may be extended out of and retracted into the distal end of the shaft. The distal end of the medical device may include, for example, a biopsy forceps, a grasper, a basket, a snare, a probe, scissors, a retrieval device, a laser, and/or any other suitable tools for, e.g., removing kidney stones.

Aspects of an exemplary ureteroscope and an exemplary medical device are described above and described below. As noted above, some of the FIGS. illustrate, amongst other things, mathematical modelling of ureteroscope irrigation. Such mathematical modeling is also described in detail below. In some embodiments, the modelling provides data that may be used to accurately and precisely control ureteroscope irrigation. For example, the modelling may provide data on ureteroscope design that may help a user design, select, and/or operate a ureteroscope (the data including, e.g., the cross-sectional area of the working channel, the cross-sectional shape of the working channel, the curvature of the shaft, material properties of the shaft, surface properties of the working channel, and/or any other aspects that may affect the flow of irrigation fluid through the working channel) and/or data on medical device design that may help a user design, select, and/or operate a medical device for use in the ureteroscope (the data including, e.g., the cross-sectional area of the insertion portion of the medical device, the cross-sectional shape of the insertion portion, material properties of the insertion portion, outer surface properties of the insertion portion, position/orientation of the insertion portion in the working channel, and/or any other aspects that may affect the flow of irrigation fluid through the working channel). Additionally or alternatively, the modelling may provide data that may help a user determine how much irrigation fluid is flowing through the working channel, to ensure that a desired level of irrigation fluid flow (e.g., an optimum flow velocity, flow rate, flow volume, or one in a desired range) is provided to a target area. Based on the data, the user, and/or a control system, may set/adjust operational parameters of a pump or other fluid source, modify aspects of the working channel, and/or modify aspects of the medical device, to achieve the desired level of irrigation fluid flow. Other types of devices may be substituted for the ureteroscope, including, as example, a hysteroscope, a uteroscope, a bronchoscope, a cystoscope, an endoscope, a colonoscope, and similar devices.

Figure 10:
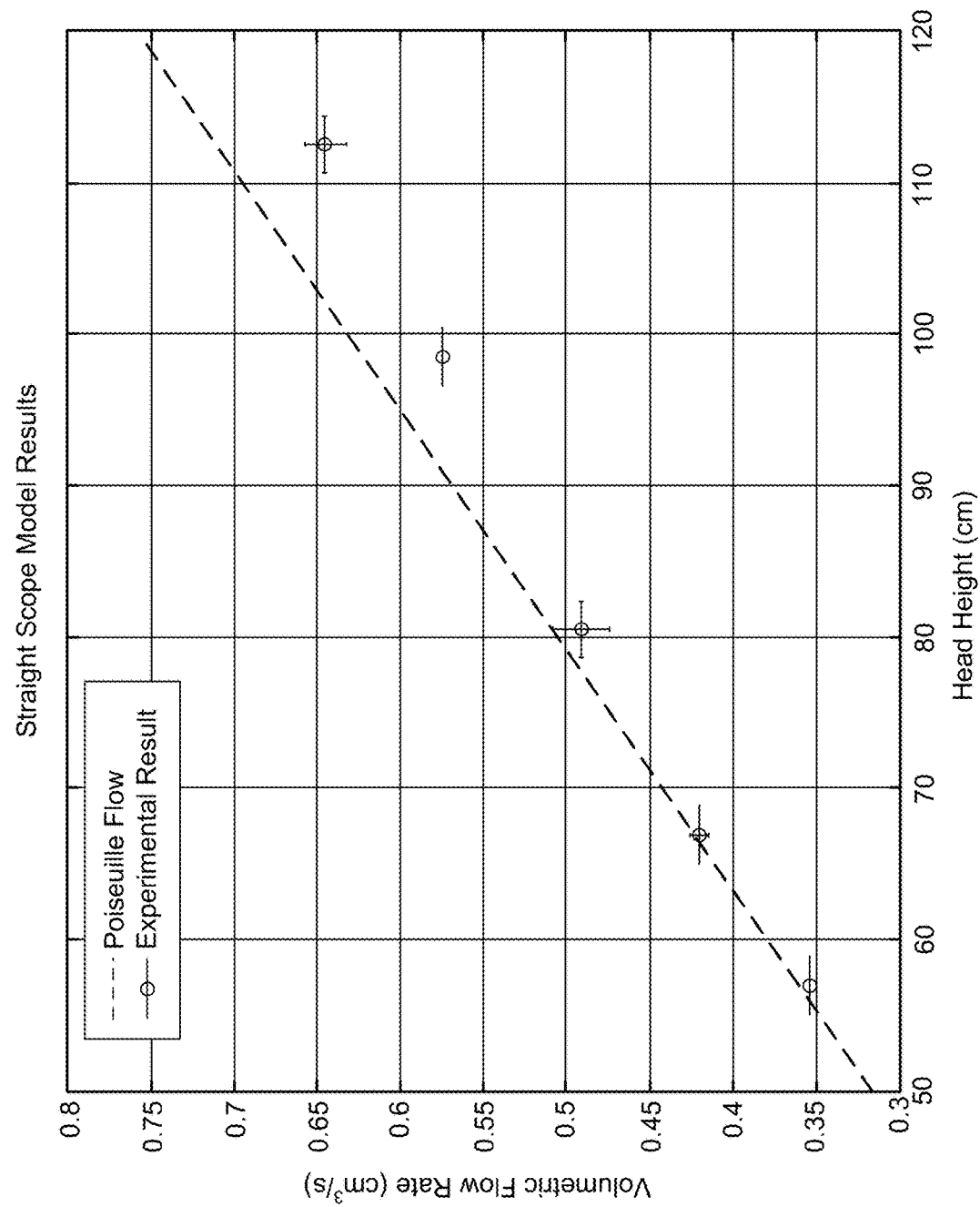
FIG. 10 illustrates the flow through a scope.
Figure 11:
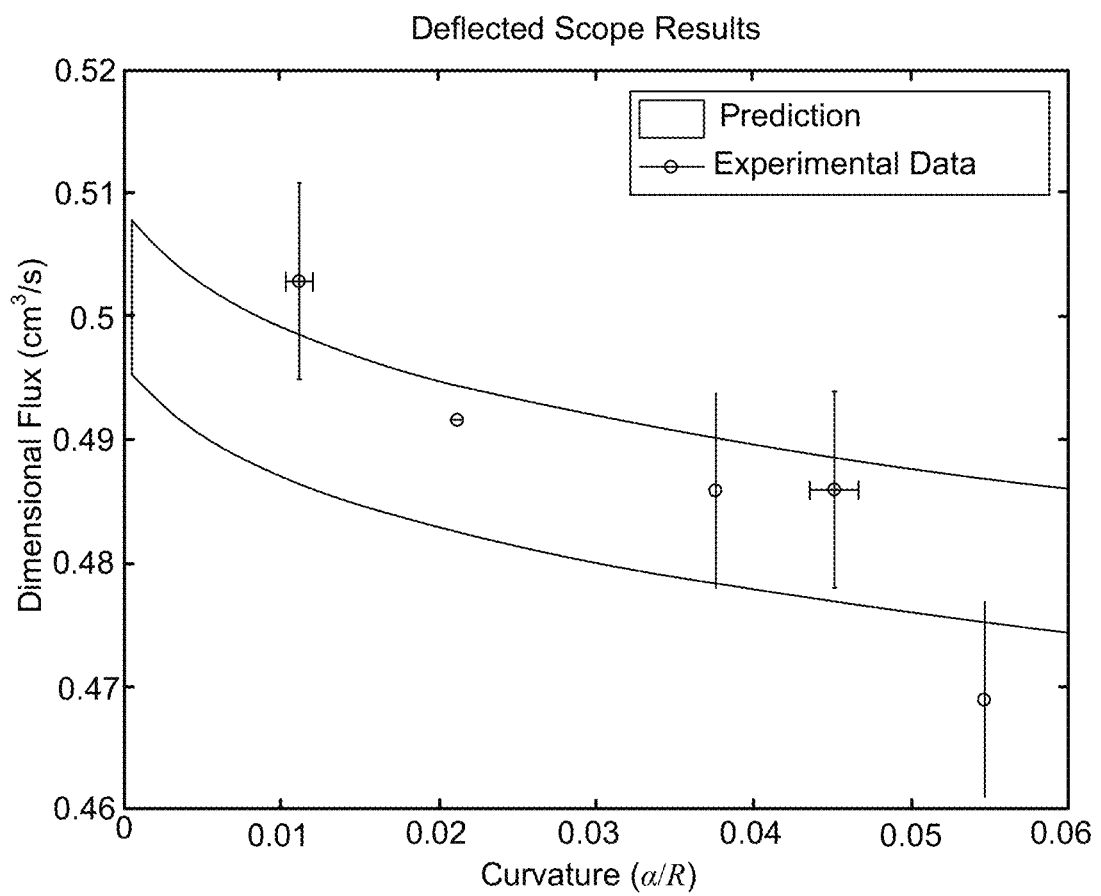
FIG. 11 illustrates the flow through a curved scope.
Figure 12:
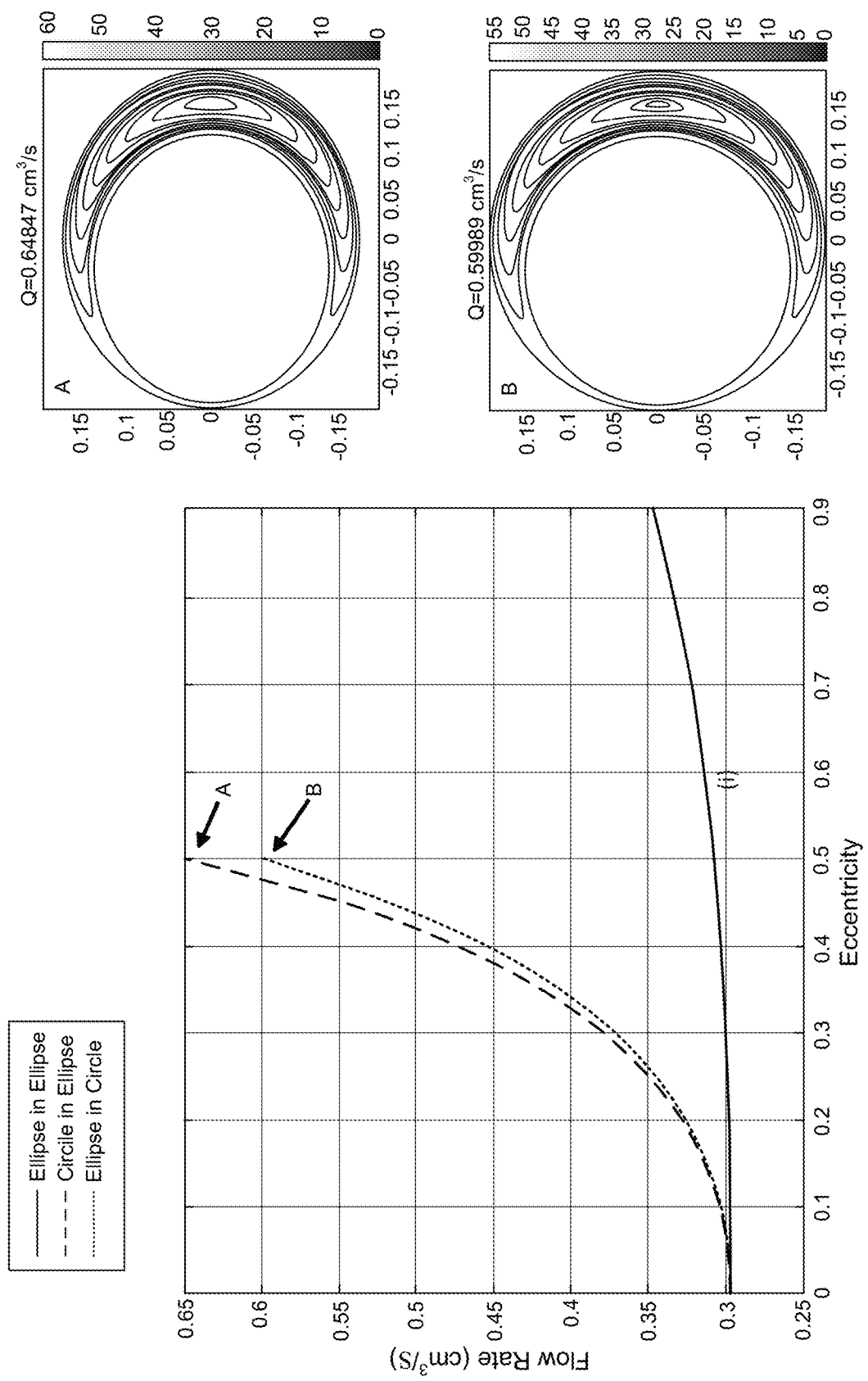
FIG. 12 illustrates the flow rate of different cross-sectional shapes of scopes and tools.
Figure 13:
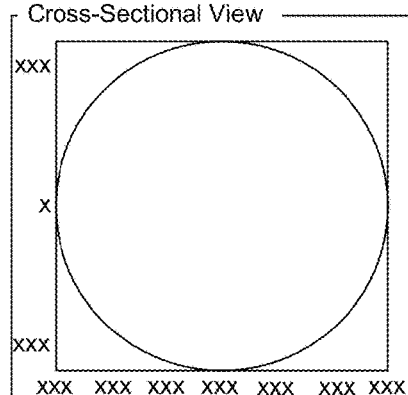
FIG. 13 illustrates a graphical user interface.
Figure 14:
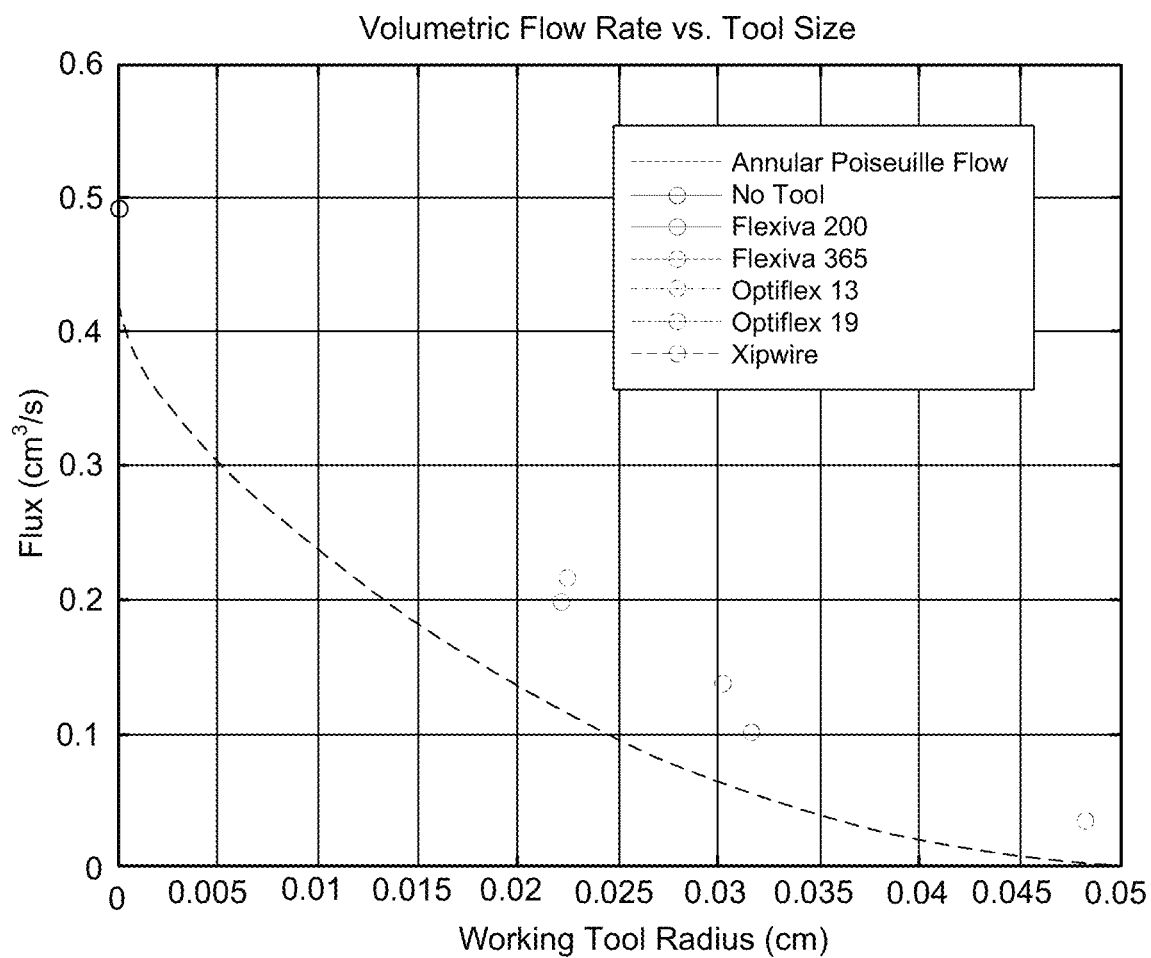
FIG. 14 illustrates a plot depicting the change in volumetric flow rate with increasing working tool size.

FIG. 10 illustrates the flow or fluid flow through a scope. There is a larger deviation at higher head heights. FIG. 11 illustrates the flow or fluid flow through a curved scope. Flow rate decreases slightly with curvature. FIG. 12 illustrates the flow rate of different cross-sectional shapes of scopes and tools.

The modelling may be performed by any suitable computing system, including, e.g., a desktop computer, a laptop, a smartphone, and the like. The computing system may be in operative communication with the fluid supply to set/adjust operating parameters of the fluid supply based on the modelling. It is also contemplated that the computing system may include one or more input devices for identifying the ureteroscope and/or the medical device, automatically (e.g., via RFID, bar code scanning, etc.) or otherwise, and may perform modelling, and take other actions (e.g., set/adjust fluid flow, send an alert, or perform any other suitable task) based on the received inputs. Additionally or alternatively, a graphical user interface (GUI), as illustrated in FIG. 10, may be used to receive data for use in the modelling and/or convey data to the user.

1 Modeling

Flow of irrigation through a uterescope with a working tool located within the channel is considered. Modelling of this set-up assumes that the tool lies concentrically within the working channel, which motivates a simple annular Poiseuille flow model driven by a hydrostatic pressure head generated by the height of the bag of irrigation fluid. This model takes the form:

$$Q = \frac{\pi(r_o^2 - r_{wt}^2)\rho g h}{8L\mu}\left[r_o^2 + r_i^2 - \frac{(r_o^2 - r_i^2)}{\log\left(\frac{a}{r_i}\right)}\right]. \quad (1)$$

Here, Q is the volumetric flow rate, $r_o$ is the radius of the working channel, $r_i$ is the radius of the working tool, h and L are the height of the saline bag and length of the scope, respectively, and p and μ are the density and viscosity of the irrigation fluid, respectively. When the predictions obtained from this mathematical model are compared with wet-lab data, there may be a discrepancy between the two curves, an example of which is shown in FIG. 11. FIG. 11 illustrates a plot depicting the change in volumetric flow rate with increasing working tool size.

In some instances, the mathematical model, equation (1), under-predicts the measured flow rate. Under-prediction of the measured data may result from the assumption that the tool lies concentrically within the working channel. Here, we reconsider the initial assumption by allowing the working tool to lie non-centrically within the channel to understand the effect of this offset.

2 Governing Equations

To derive the simple formula given by equation (1), we considered steady, unidirectional flow in an annulus. Here, we recall a brief derivation of this.

2.1 Navier Stokes

The Navier Stokes equations for an incompressible fluid are $$\nabla \cdot u = 0, \quad (2)$$

$$\rho\left[\frac{\partial u}{\partial t} + (u \cdot \nabla)u\right] = -\nabla p + \mu \nabla^2 u, \quad (3)$$

where $u=(u_x, u_y, u_z)$ describes the flow in the x, y, and z directions, and ρ and μ are the density and viscosity of the irrigation fluid.

2.2 Steady State, Unidirectional Flow

Some systems are steady-state systems. In such systems there is no dependence on time; thus we can ignore the time derivative in equation (3). We also assume that the flow is unidirectional in the axial direction along the scope, $u_z$, and so $u_x=u_y=0$. Thus, the Navier Stokes equations becomes $$\frac{\partial u_z}{\partial z} = 0, \quad (4)$$

$$0 = \frac{\partial p}{\partial z} + \mu\left[\frac{\partial^2 u_z}{\partial x_2} + \frac{\partial^2 u_z}{\partial y^2}\right], \quad (5)$$

along with ∂p/∂x=∂p/∂y=0. Writing (5) in the form $$\frac{1}{\mu}\frac{dp}{dz} = \frac{\partial^2 u_z}{\partial x^2} + \frac{\partial^2 u_z}{\partial y^2}, \quad (6)$$

we see that the LHS is independent of x and y and the RHS is independent of z (because the relevant partial derivatives are zero). Thus, the pressure gradient, dp/dz, must be a constant. We will henceforth denote $u:=u_z$ for notational simplicity.

2.3 Boundary Conditions

We begin by modelling the cross-sections of the working tool and working channel as a pair of non-concentric circles, both centered on the x-axis. We denote the radius of the working tool to be $r_i$ (inner) and the radius of the working channel to be $r_o$ (outer), where we note that $r_i<r_o$. The corresponding center coordinates of the tool and channel we set to be $(w_i, 0)$ and $(w_o, 0)$, respectively. Without loss of generality, we will assume $w_i<w_o$, so the center of the inner circle is shifted to the left of the center of the outer circle. Thus, imposing no-slip conditions on both the outer surface of the working tool and the inner surface of the working channel, we have the boundary conditions $$u(x_i,y_i)=0 \,\forall (x_i,y_i) s.t. (x_i-w_i)^2+y_i^2=r_i^2 \quad (7)$$

$$u(x_o,y_o)=0 \,\forall (x_o,y_o) s.t. (x_o-w_o)^2+y_o^2=r_o^2, \quad (8)$$

where we recall that $(x-w)^2+y^2=r^2$ is the equation for a circle of radius r, centered at (w, 0).

3 Transformation to Bipolar Coordinates

Previously, when solving (6) to obtain the annular flow solution (1), we utilized a polar coordinate system, motivated by the rotational symmetry of the geometry which resulted from the concentric nature of the inner and outer circles.

Figure 15:
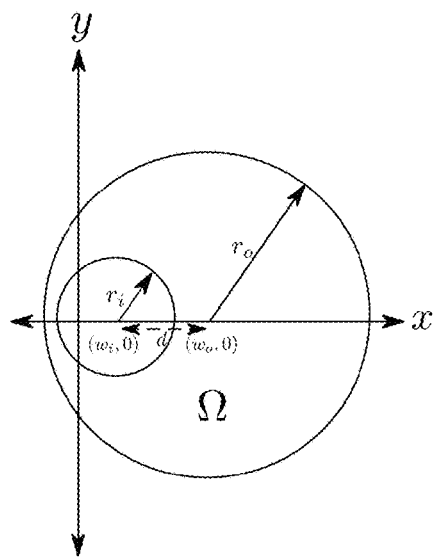
FIG. 15 illustrates the geometry over which we aim to solve (6).

FIG. 15 illustrates the geometry over which we aim to solve (6). Here the domain, Ω, represents the space between the inner and outer circles (the tool and working channel, respectively).

We now aim to solve (6) over the domain Ω, depicted in FIG. 15. To do this, we utilize the bipolar coordinate system (η,ξ), related to Cartesian coordinates by $$x = \frac{c\sinh\eta}{\cosh\eta - \cos\xi}, \quad (9)$$

$$y = \frac{c\sin\xi}{\cosh\eta - \cos\xi}. \quad (10)$$

Here, we will show that lines of constant η represent offset circles centered on the x-axis in Cartesian coordinates, and lines of constant ι correspond to offset circles centered on the y-axis. We assume that the inner and outer circles in our domain are centered on the x-axis, and will thus correspond to constant η values. The ξ coordinate varies from 0 to 2π, and behaves similarly to an angular coordinate in polar coordinates.

3.1 Converting the Domain

To describe circular boundaries, such as those in FIG. 15, in bipolar coordinates, we first consider the general formulation of a circle with radius r, centered at (w, 0), in Cartesian coordinates $$(x-w)^2+y^2=r^2, \quad (11)$$

or equivalently $$x^2+y^2+w^2-r^2=2xw. \quad (12)$$

To manipulate the expressions relating Cartesian and bipolar coordinates to resemble this form, we first solve (9) for cos ξ to obtain $$\cos\xi = \cosh\eta - \left(\frac{c}{x}\right)\sinh\eta. \quad (13)$$

Dividing (9) by (10) we also have $$\frac{x}{y} = \frac{\sinh\eta}{\sin\xi},$$

and solving for $\sin\xi$ we get $$\sin\xi = \sinh\eta\left(\frac{y}{x}\right)^2. \qquad (14)$$

Now, utilizing the expressions (13) and (14) within the identity $\sin^2\xi + \cos^2\xi = 1$ we find that $$x^2 + y^2 + c^2 = 2xc\coth\eta. \qquad (15)$$

Thus, comparing (15) with (12), we see immediately that the coordinate of the circle's center is given by $$w = c\coth\eta. \qquad (16)$$

Again relating (15) with (12), we also have that $w^2 - r^2 = c^2$. Hence, using (16), we can rearrange to obtain $$r = \frac{c}{|\sinh\eta|}. \qquad (17)$$

Therefore, lines of constant $\eta$ represent circles in Cartesian coordinates with radius $c/\sinh\eta$, centered at $(c\coth\eta, 0)$. For the inner and outer circles in our domain we introduce values of constant $\eta$, namely $n_i$ and $n_o$, respectively, such that $$r_i = \frac{c}{|\sinh\eta_i|}, w_i = c\coth\eta_i, \qquad (18)$$

$$r_o = \frac{c}{|\sinh\eta_o|}, w_o = c\coth\eta_o. \qquad (19)$$

Figure 16:
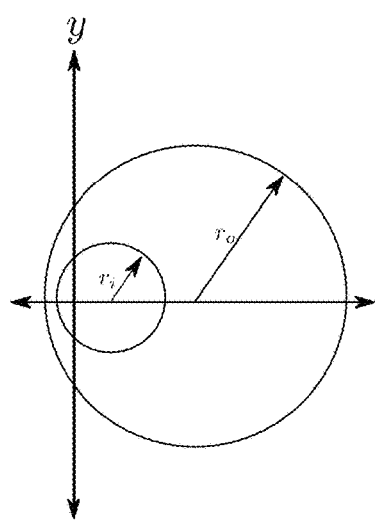
FIG. 16 is a schematic that illustrates the transformation of a smaller circle within a larger circle, both centered on the x-axis in Cartesian Coordinates, translated to bipolar Coordinates.
Figure 16:
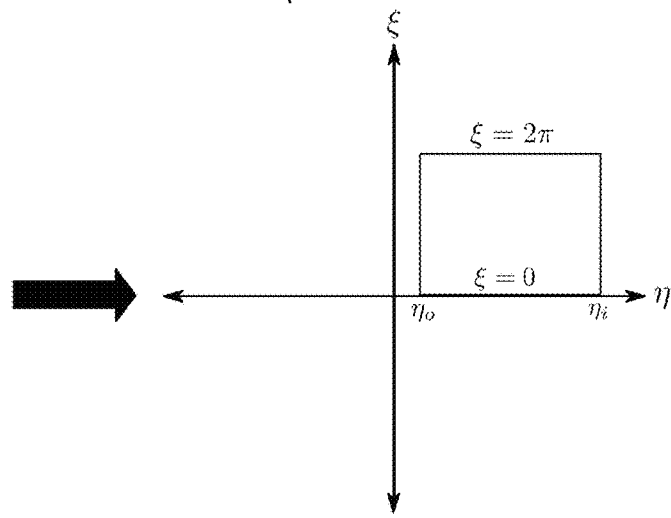

FIG. 16 is a schematic that illustrates the transformation of a smaller circle within a larger circle, both centered on the x-axis in Cartesian Coordinates, translated to bipolar Coordinates.

We note here that from (17), we see that circles with larger radii correspond to smaller values of $\eta$, and hence $\eta_o < \eta_i$. From the definitions (18) and (19), it follows that $$c = r_i|\sin h\eta_i| = r_o|\sin h\eta_o|. \qquad (20)$$

Therefore, our domain $\Omega$, corresponds to $\eta_o \leq \eta \leq \eta_i$, and $0 \leq \xi \leq 2\pi$, and this transformation of the domain from Cartesian to bipolar coordinates is depicted graphically in FIG. 16. We now consider the distance between the two centers, which we will denote as $d = w_o - w_i$, labelled as such in FIG. 15. Restricting the values $\eta_i$, $\eta_o > 0$, and hence $\sin h\eta_i$, $\sin h\eta_o > 0$, we have, using (16), that $$d = r_o\cos h\eta_o - r_i\cos h\eta_i. \qquad (21)$$

Using (20) and (21), along with the identity $\cos h^2\eta_o - \sin h^2\eta_o = 1$, we obtain $$\cosh\eta_i = \frac{r_o^2 - r_i^2 - d^2}{2dr_i} \qquad (22)$$

Similarly, with the identity $\cos h^2\eta_i - \sin h^2\eta_i = 1$ we obtain $$\cosh\eta_o = \frac{r_o^2 - r_i^2 - d^2}{2dr_o}. \qquad (23)$$

Defining Dimensionless Parameters $$\phi = \frac{d}{r_o - r_i}, \qquad (24)$$

$$\gamma = \frac{r_i}{r_o}, \qquad (25)$$

we can represent (22) and (23) as $$\cosh\eta_i = \frac{1}{\gamma}\frac{\gamma(1+\phi^2)+(1-\phi^2)}{2\phi}, \qquad (26)$$

$$\cosh\eta_o = \frac{\gamma(1-\phi^2)+(1+\phi^2)}{2\phi}, \qquad (27)$$

providing us with expressions for $\eta_i$ and $\eta_o$ in terms of the geometric properties of the circles.

4 Circular Geometries

We now analyze the effect of offsetting the tool in the working channel using bipolar coordinates. Here, we consider the cross-sections of the working tool and channel to be circular, and in the next section we will extend this analysis to elliptical geometries.

4.1 Converting the Equation

We will now express the equation for steady, unidirectional flow (6) in bipolar coordinates. To do this, we first consider the position of an arbitrary point in (x, y) space, which can be characterized in terms of $(\eta, \xi)$ by $$r = \frac{c\sinh\eta}{\cosh\eta - \cos\xi}i + \frac{c\sin\xi}{\cosh\eta - \cos\xi}j. \qquad (28)$$

To express the Laplacian of a scalar field in a curvilinear coordinate system, such as bipolar coordinates, we define scale factors $h_\eta = |\partial r/\partial\eta|$, $h_\xi = |\partial r/\partial\xi|$, and $h_z = |\partial r/\partial z|$ and use the formula $$\nabla^2\Phi = \frac{1}{h_\eta h_\xi}\left[\frac{\partial}{\partial\eta}\left(\frac{h_\xi h_z}{h_\eta}\frac{\partial\Phi}{\partial\eta}\right) + \frac{\partial}{\partial\xi}\left(\frac{h_z h_\eta}{h_\xi}\frac{\partial\Phi}{\partial\xi}\right)\right], \qquad (29)$$

derived in (1). For the bipolar coordinate system, we compute the scale factors to be $$h_\eta = h_\xi = \frac{c}{\cosh\eta - \cos\xi}. \qquad (30)$$

Thus, applying the operator conversion formula given by (29), the governing equation (6) becomes $$\frac{\partial^2 u}{\partial \eta^2} + \frac{\partial^2 u}{\partial \xi^2} = \frac{c^2}{\mu(\cosh\eta - \cos\xi)^2} \frac{dp}{d\xi}, \quad (31)$$

where we recall that dp/dz is a constant pressure gradient.

4.2 Boundary Conditions

The no-slip boundary conditions are now given in bipolar coordinates as $$u(\eta, \xi) = 0 \text{ on } \eta = \eta_i, \eta_o. \quad (32)$$

We now require two additional boundary conditions in terms of $\xi$, and due to the line of symmetry along the x-axis we can reduce the size of the domain to $0 \leq \xi \leq \pi$ with the conditions $$\frac{\partial u}{\partial \xi}(\eta, \xi) = 0 \text{ on } \xi = 0, \pi, \quad (33)$$

which allows for the desired symmetric velocity profiles.

4.3 Solving the Equation: Finite Difference Scheme

Figure 17:
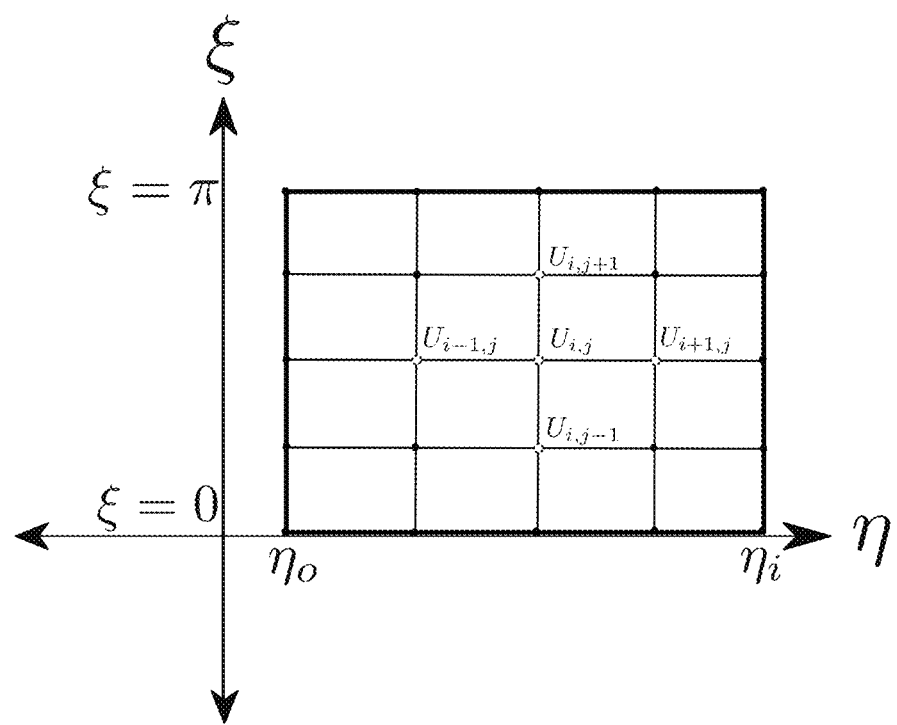
FIG. 17 is a schematic of the discretization of the domain.

To solve (31) numerically, we first discretize the rectangular $(\eta, \xi)$ domain as shown in FIG. 17. As an illustrative example, we have chosen the number of points in $\eta$, $(n_\eta)$, and in $\xi$ $(n_\xi)$, to be 5. The corresponding spatial steps, $h_\eta$ and $h_\xi$, are calculated as $h_\eta = (\eta_i - \eta_o)/(n_\eta - 1)$ and $h_\xi = \pi/(n_\xi - 1)$. FIG. 17 is a schematic of the discretization of the domain.

We then approximate the partial derivatives in equation (31) by finite differences, in order to construct a linear system. Using central difference approximations, we can approximate (31) by $$\frac{U_{i+1,j} - 2U_{i,j} + U_{i-1,j}}{h_\eta^2} + \frac{U_{i,j+1} - 2U_{i,j} + U_{i,j-1}}{h_\xi^2} = \frac{c^2}{[\cosh((i-1)h_\eta + \eta_2) + \cos((j-1)h_\xi)]^2} \frac{dp}{dz}, \quad (34)$$

Where $U_{i,j}$ is the numerical approximation of u $((i-1)h_\eta + \eta_o, (j-1)h_\xi)$ The discretization of the domain is demonstrated in FIG. 17. Multiplying (34) through by $h_\eta^2 h_\xi^2$, we obtain the following equation $$[-2(h_\xi^2 + h_\eta^2)]U_{i,j} + h_\xi^2 U_{i+1,j} + h_\xi^2 U_{i-1,j} + h_\eta^2 U_{i,j+1} + h_\eta^2 U_{i,j-1} = \frac{h_\eta^2 h_\xi^2}{[\cosh((i-1)h_\eta + \eta_o - \cos(j-1)h_\xi)]^2}. \quad (35)$$

This can be represented as a linear system of the form $$Au = b, \quad (36)$$

where $u = [U_{1,1}, U_{2,1}, \ldots, U_{n_\eta,1}, U_{1,2}, \ldots U_{n_\eta,n_\xi}]$. We apply the no-slip boundary conditions (32) by directly imposing that $$U_{1,j} = U_{n_\eta,j} = 0 \text{ for } i=1, \ldots, n_\xi, \quad (37)$$

and we approximate the symmetric boundary conditions (33) with $$U_{1,j+1} - U_{1,j} = U_{n_\xi,j+1} - U_{n_\xi,j} = U_{n_\xi,j} - U_{n_\xi,j-1} \text{ for } j=1, \ldots, n_\eta, \quad (38)$$

where (38) is obtained from a one-sided approximation to the first-order derivatives. Thus, it only remains to solve for the interior points in FIG. 17, and thus A is an N×N pentadiagonal matrix (where $N = n_\eta n_\xi - 2n_\eta - 2n_\xi + 4$) containing the coefficients given by the left-hand side of (35), and the vector b contains the right-hand side values from (35) for $i = 2, \ldots, n_\eta - 1$, $j = 2, \ldots, n_\xi - 1$.

4.4 Solving the Equation: Analytical Solution

An analytical solution to (31), describing fully developed flow in an eccentric annulus is presented in [2] as $$u = -\frac{c^2}{\mu}\frac{dp}{dz}\left[F + E\eta - \frac{\coth\eta}{2} + \sum_{n=1}^{\infty}\{A_n \exp(n\eta) + (B_n - \coth\eta)\exp(-n\eta)\}\cos n\xi\right], \quad (39)$$

where $$F = \frac{\eta_i \coth\eta_i - \eta_o \coth\eta_i}{2(\eta_i - \eta_o)},$$

$$E = \frac{\coth\eta_i - \coth\eta_o}{2(\eta_i - \eta_o)},$$

$$A_n = \frac{\coth\eta_i - \coth\eta_o}{\exp(2n\eta_i) - \exp(2n\eta_o)},$$

$$B_n = \frac{\exp(2n\eta_i)\coth\eta_o - \exp(2n\eta_o)\coth\eta}{\exp(2n\eta_i) - \exp(2n\eta_o)},$$

and thus, using an approximation to the infinite sum, we can compare this against our numerical solution to validate the result.

4.5 Results: Velocity Profiles

Figure 18:
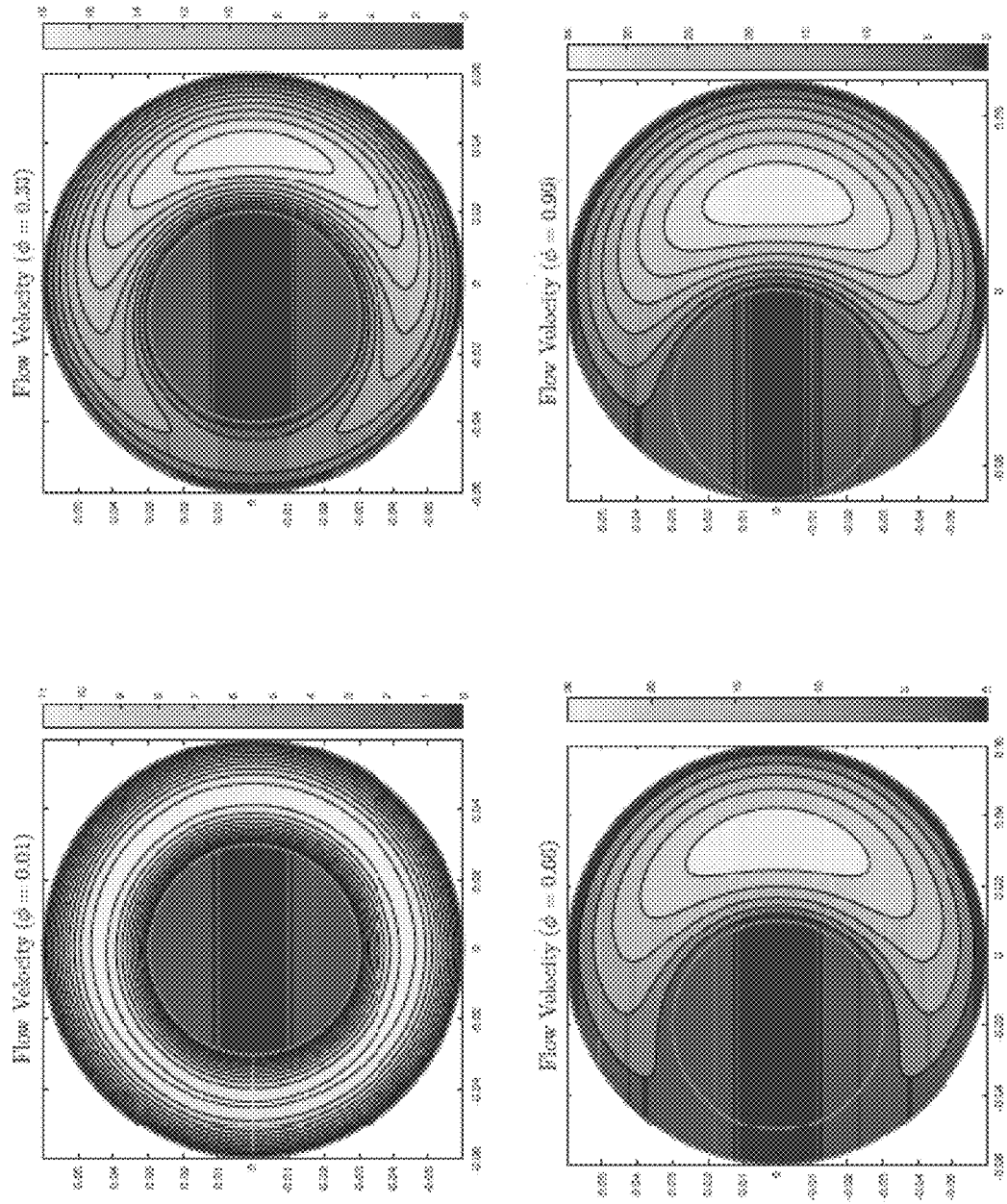
FIG. 18 illustrates flow velocity profiles for $r_1=0.03$, $r_2=0.06$, and $\varphi$ varying from 0.01 to 0.99. The domain is shifted such that the outer circle is centered at (0, 0).

After constructing the linear system described in the previous section, we solve Au=b for the velocity at the discrete points. After converting the corresponding $(\eta, \xi)$ values back to Cartesian (x, y), we can plot the resulting velocity profiles. In order to display this as a continuous color map, we implement MATLAB's grid data function, which linearly interpolates the solution over a grid of the x and y values for which the equation was solved. Here we consider the effect of varying the offset parameter $\varphi$ on the resulting distribution of flow velocity in the domain. FIG. 18 illustrates flow velocity profiles for $r_1 = 0.03$, $r_2 = 0.06$, and $\varphi$ varying from 0.01 to 0.99. We have shifted the domain so the outer circle is centered at (0, 0).

We see from FIG. 15 that the maximum velocity obtained increases with increasing $\varphi$. Intuitively this correlates with an increasing maximum distance between the two boundaries where there is zero velocity, providing a larger region for the flow to develop. The velocity profiles generated using the analytical solution (39) with fifty terms of the infinite sum display good qualitative agreement with the numerical results.

4.6 Results: Volumetric Flow Rate

The volumetric flow rate, Q, is calculated by integrating the velocity over the domain. Thus, we have that $$Q = \int_{\eta_o}^{\eta_i}\int_0^{2\pi}\left|\frac{\partial(x,y)}{\partial(\eta,\xi)}\right|u d\eta d\xi = 2c^2 \int_{\eta_o}^{\eta_i}\int_0^\pi \left(\frac{1}{\cosh\eta - \cos\xi}\right)^2 u d\eta d\xi. \quad (40)$$

We can use MATLAB's trapz which implements the Trapezoidal Rule, to approximate this integral numerically.

Figure 19A:
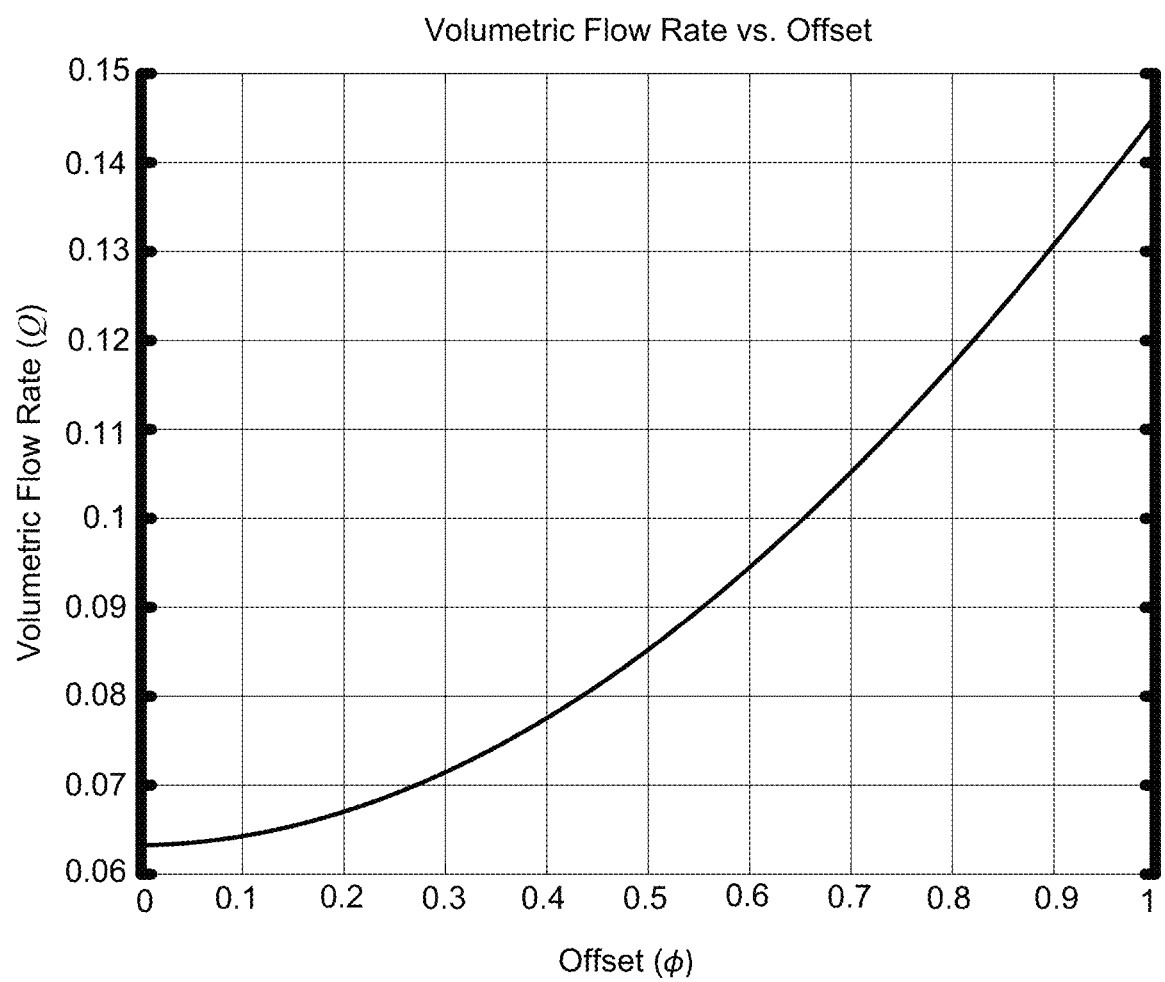
FIGS. 19A and 19B illustrate volumetric flow rate results from the offset model.

FIG. 19A illustrates the effect of shifting the working tool from the center to the edge of the channel on the volumetric flow rate. Here $r_1 = 0.03$ cm, $r_2 = 0.06$ cm, h = 79.5 cm.

Figure 19B:
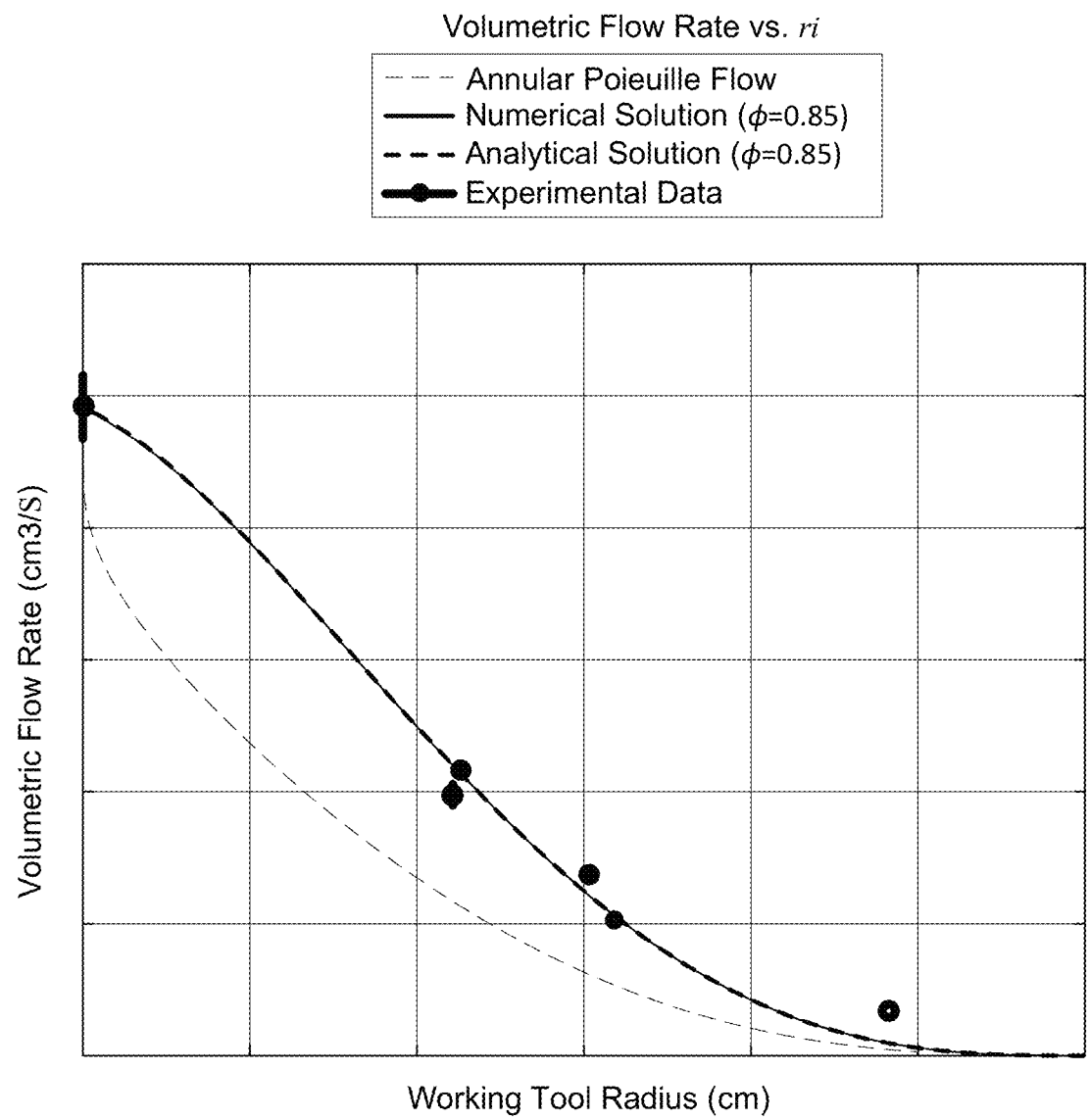

FIG. 19B illustrates the change in volumetric flow rate with increasing working tool size for the numerical and analytical solutions of the offset model. This is compared with experimental data, as well as with the concentric model.

Figure 28:
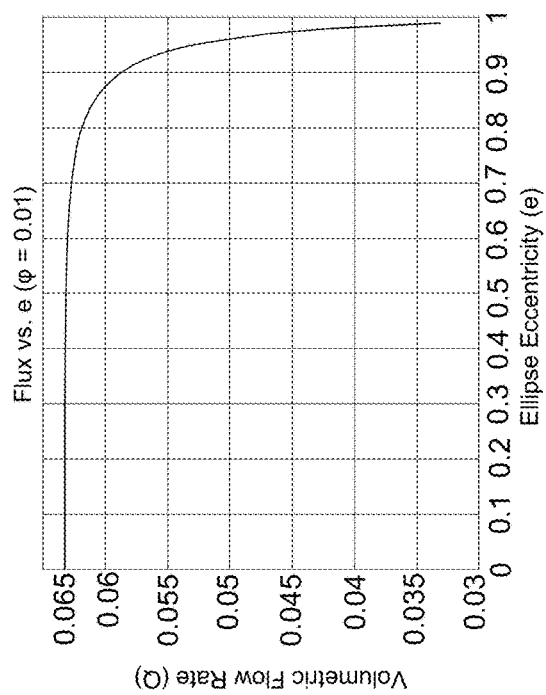

The increase in volumetric flow rate as φ varies from 0.01 to 0.99, shown in FIG. 16B, correlates with an increase in maximum velocity, shown in FIG. 28. Thus, for the parameters used, as the working tool is shifted from the center to the edge of the working channel, we achieve approximately a 130% increase in volumetric flow rate. In FIG. 6A, which shows the decrease in volumetric flow rate with working tool size, the comparison between the numerical and analytical solutions of the offset model are displayed for φ=0.85. These are compared against the experimental data and the original concentric prediction, as shown in FIG. 11. We see that this updated mathematical model that considers the tool as offset within the channel, gives a much better prediction of the experiments than the concentric model. Here an offset of φ=0.85 has been chosen, as it displays a good fit with the experimental data. In FIG. 16B we also see good agreement between the analytical solution (39) and the numerical solution obtained by solving the finite difference scheme.

5 Elliptical Geometries

Figure 20:
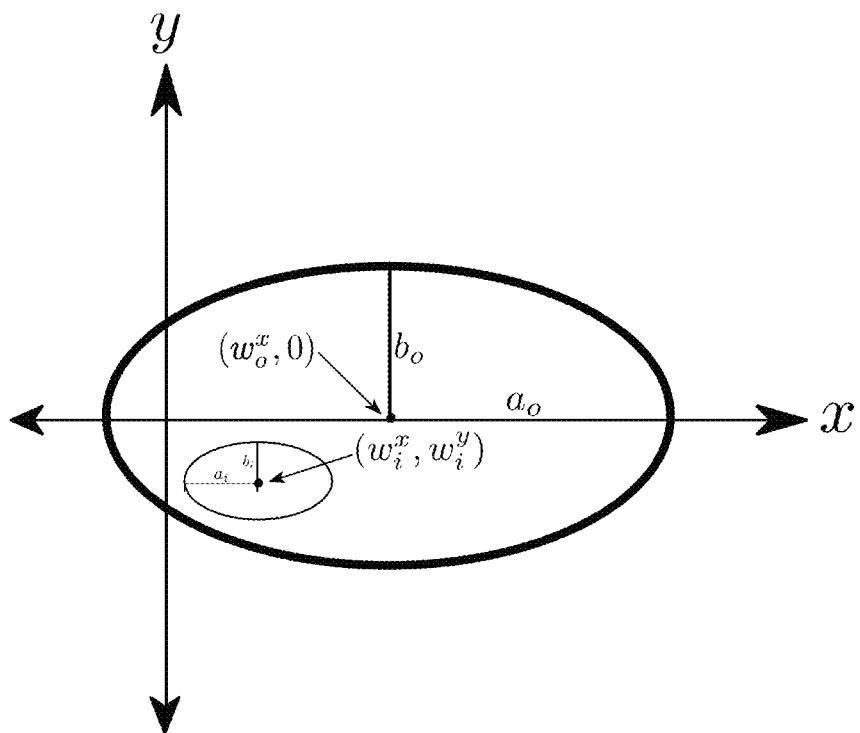
FIG. 20 is a diagram of the geometry we wish to solve over in Cartesian coordinates. The eccentricity of the inner and outer ellipses is identical, so $a_i/b_i = a_o/b_o = \sqrt{1-e^2}$.

We now consider the effect of modifying the cross-sectional shape of the working channel and working tool to be elliptical instead of circular. The eccentricity of an ellipse relates its major and minor axes, and thus describes how 'squashed' it is. An eccentricity value of zero describes a circle, and as this value increases, the shape tends to an infinitely long and thin horizontal ellipse. We consider the tool and channel to be ellipses of the same eccentricity, e, with respective major and minor axes $a_i$ and $b_i$ for the tool and $a_o$ and $b_o$ for the channel. FIG. 20 demonstrates this domain in Cartesian coordinates. We note that as this geometry is no longer rotationally symmetric, it is no longer generalizable to consider both tool and channel as centered along the x axis, and thus, we allow for the center of the inner ellipse to be located anywhere within the outer channel. However, for simplicity, we maintain the orientation of the inner ellipse, i.e., the respective axes of the inner and outer geometries remain parallel.

FIG. 20 is a diagram of the geometry we wish to solve over in Cartesian coordinates. Here the eccentricity of the inner and outer ellipses is identical, so $a_i/b_i = a_o/b_o = \sqrt{1-e^2}$.

Using the formula for an ellipse with given center, major, and minor axes, we can write the equations describing the inner and outer ellipses shown in FIG. 20. The inner ellipse is given by $$\frac{(x-w_i^x)^2}{a_i^2} + \frac{(y-w_i^y)^2}{b_i^2} = 1, \tag{41}$$

and the equation for the outer ellipse is $$\frac{(x-w_o^x)^2}{a_o^2} + \frac{y^o}{b_o^2} = 1. \tag{42}$$

We aim to solve our governing equation (6) with finite differences in this modified domain, and thus we will transform the elliptical geometry in order to represent it as a rectangular y domain in bipolar coordinates (η,ξ) as before. To obtain a geometry analogous to that shown in FIG. 21, we scale the axes to transform the ellipses to circles, and then rotate this new coordinate system so the center of the tool is located along the x axis of the new coordinate system. Hence, we introduce the change of variables $$\tilde{x} = x\cos\theta - \frac{\sin\theta}{\sqrt{1-e^2}}y - w_o^x\cos\theta + w_o^x \tag{43}$$

$$\tilde{y} = x\sin\theta + \frac{\cos\theta}{\sqrt{1-e^2}}y - w_o^x\sin\theta, \tag{44}$$

Where $$\theta = \arctan\left[\frac{w_i^y}{(w_i^x - w_o^x)\sqrt{1-e^2}}\right], \tag{45}$$

which is the angle we rotate the coordinates after scaling the y axis. In terms of these new coordinates, the equations representing the ellipses become $$(\tilde{x}-w_o^x)^2 + \tilde{y}^2 = a_o^2 \tag{46}$$

For the outer ellipse, and $$|(\tilde{x}-(\omega_o-(\omega_o-w_i^x)\sec\theta))^2 + \tilde{y}^2 = a_i^2 \tag{47}$$

for the inner ellipse. We can see from these equations that in the (x̃, ỹ) coordinate system, the inner and outer ellipses are represented by circles of radii $a_o$ and $a_i$, respectively, both centered along the x axis. This new geometry is shown in FIG. 21, and we can now represent the boundaries as constant η values in bipolar coordinates.

Figure 21:
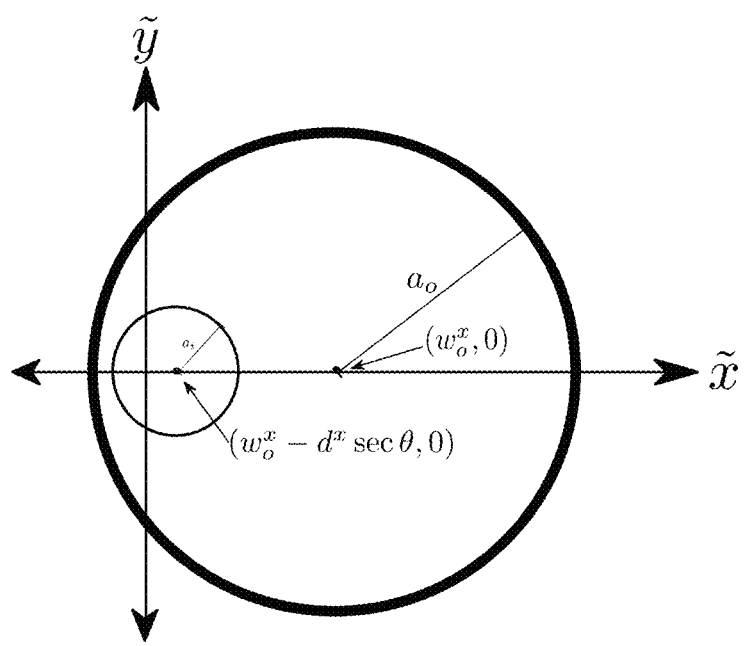
FIG. 21 is a diagram of the transformed geometry. Here $d^x = w_o^x - w_i^x$ (the distance between the x coordinates of the centers of the ellipses) and $\theta = \arctan[w_i^y/((w_i^x - w_o^x)\sqrt{1-e^2})]$ gives the angle that the inner ellipse (after it has been transformed to a circle) has to be rotated for its center to lie on the ~x axis.

FIG. 21 is a diagram of the transformed geometry. Here $d^x = w_o^x - w_i^x$ (the distance between the x coordinates of the centers of the ellipses) and $\theta = \arctan[w_i^y/((w_i^x-w_o^x)\sqrt{1-e^2})]$ gives the angle that the inner ellipse (after it has been transformed to a circle) has to be rotated for its center to lie on the x̃ axis.

5.1 Converting the Equation

We now represent the governing equation (6) in terms of (x̃, ỹ), given by (43), to obtain $$(\cos^2\theta + k^2\sin^2\theta)\frac{\partial^2 u}{\partial \tilde{x}^2} + (\sin^2\theta + k^2\cos^2\theta)\frac{\partial^2 u}{\partial \tilde{y}^2} = \frac{1}{\mu}\frac{dp}{dz}, \tag{48}$$

where $k=1/(1-e^2)$. Transforming (48) into bipolar coordinates, defined by (9) and (10), we have the following elliptic partial differential equation $$\alpha\frac{\partial^2 u}{\partial \eta^2} + 2\beta\frac{\partial^2 u}{\partial \eta \partial \xi} + \gamma\frac{\partial^2 u}{\partial \xi^2} + \Delta_1\frac{\partial u}{\partial \eta} + \Delta_2\frac{\partial u}{\partial \xi} = \frac{c^2}{\mu}\frac{dp}{dz}, \tag{49}$$

where α, β, γ, $\Delta_1$, and $\Delta_2$, are functions of η and ξ given by

α(η,ξ)=(cos ξ cos hη−1)²(cos²θ+k² sin²θ)+sin²ξ(k² cos²θ+sin²θ)sin h²η,

β(η,ξ)=(k²−1)cos(2θ)(cos ξ cos hη−1)sin ξ sin hη,

γ(η,ξ)=(cos ξ cos hη−1)²(k² cos²θ+sin²θ)+sin² (cos²θ+k² sin²θ)sin h²η, $$\Delta_1(\eta,\xi)=(k^2-1)\cos^2\theta(\cos\xi-\cos(2\xi)\cos h\eta)\sin\eta,$$

$$\Delta_2(\eta,\xi)=(k^2-1)\cos^2\theta\sin\xi(\cos\xi\cos h^2\eta+\cos\xi\sin h^2\eta-\cos h\eta).$$

5.2 Boundary Conditions

The no-slip boundary conditions are now given in bipolar coordinates as $$u(\eta,\xi)=0 \text{ on } \eta=\eta_i,\eta_o. \tag{50}$$

As we no longer have a domain that is symmetric across the x axis, we must implement different boundary conditions in terms of and we take these to be $$u(\eta, 0) = u(\eta, 2\pi) \tag{51}$$

$$\frac{\partial u}{\partial \xi}(\eta, 0) = \frac{\partial u}{\partial \xi}(\eta, 2\pi), \tag{52}$$

which ensure periodicity of the domain with respect to $\xi$, with period $2\pi$.

5.3 Specifying a Geometry

Figure 22:
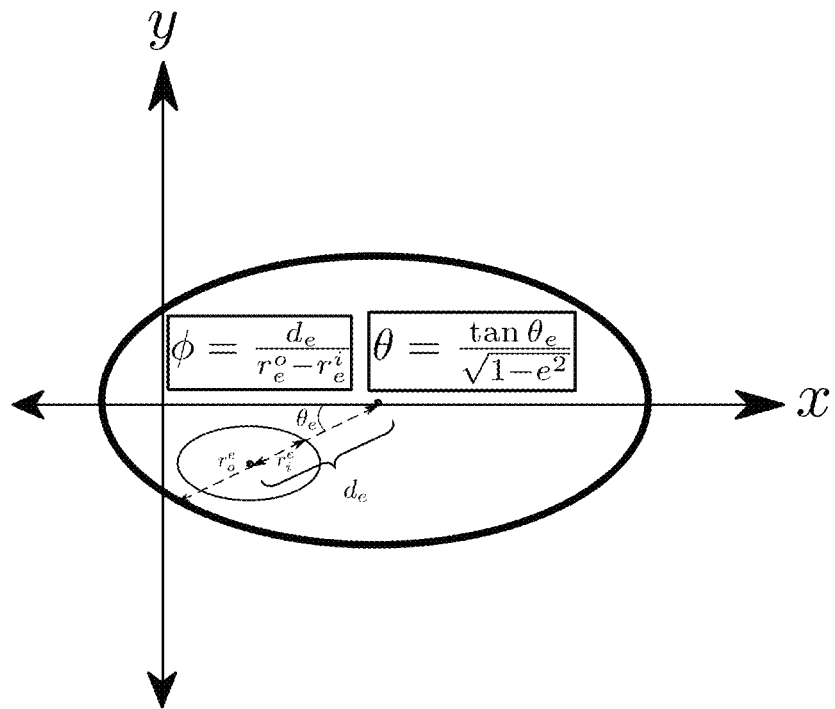
FIG. 22 is a schematic of a domain.

We can determine an elliptical geometry of the form shown in FIG. 17 by specifying three parameters, which are the eccentricity of the ellipse, e, the relative amount of offset, $\psi$r, and the angle formed between the x axis and a line connecting the ellipse centers, $\theta$e. The eccentricity is given by $$e = \sqrt{1-\left(\frac{b_i}{a_i}\right)^2} = \sqrt{1-\left(\frac{b_o}{a_o}\right)^2}, \tag{53}$$

so that for circles e=0, as $b_i$=$a_i$ and $b_o$=$a_o$=ao. The offset parameter, $\varphi$ is defined to be $$\phi = \frac{d_e}{r_e^o - r_e^i}, \tag{54}$$

where $d_e$ is the distance between the centers of the tool and channel, and $r_e^i$ and $r_e^o$ are the radii of the inner and outer ellipses, respectively, at an angle $\theta_e$, as shown in FIG. 22.

FIG. 22 is a schematic of the domain. We specify $\psi$, e, and $\theta_e$, and use these to determine $\theta$.

We find that $\psi$ (which can be interpreted as the relative distance that the ellipse is shifted from concentric along a line connecting the two ellipse centers, with respect to the maximum possible shift in this direction) is conserved through the coordinate transformation, and represents the $\psi$r used in bipolar coordinates after the change of coordinates (43). Using e, $\psi$, $\theta_e$, $a_i$, and $a_o$, we can determine $w_y$ and $w_1^x-w_2^x$ (FIG. 20), which can be used to determine $\theta$, which is the angle that the coordinate system must be rotated once the ellipses have been transformed to circles. Thus, we have the required information to perform the coordinate transformations, and hence to solve (49) in this geometric domain.

5.4 Finite Difference Scheme

We now construct a finite difference scheme to solve (49) numerically, subject to the appropriate boundary conditions (51) and (52).

Figure 23:
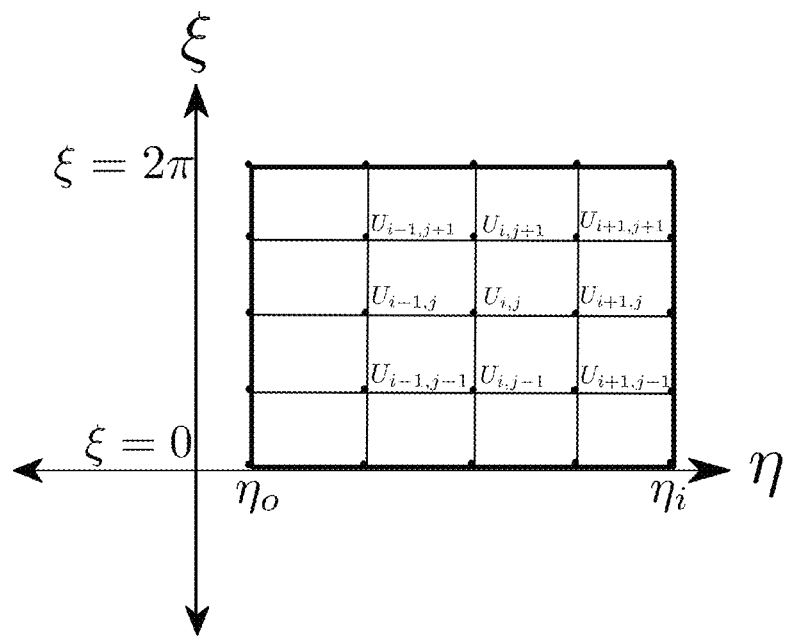
FIG. 23 is a schematic of the discretization of the domain of FIG. 22.

FIG. 23 is a schematic of the discretization of the domain. Here, changes in i represent changes in $\eta$, and incrementing j changes $\xi$.

We implement central difference approximations with a step in $\eta$ of $h_\eta=(\eta_i-\eta_o)/(n_\eta-1)$ and a step in $\xi$ of $h_\xi=2\pi/(n_\xi-1)$, where $n_\eta$ and $n_\xi$ are the number of discretization's along these two axes. We obtain the finite difference scheme $$[-2(\alpha h_\xi^2 + \gamma h_\eta^2)]U_{i,j} + \left[h_\xi^2\left(\alpha + \frac{1}{2}\Delta_1 h_\eta\right)\right]U_{i+1,j} + \left[h_\xi^2\left(\alpha - \frac{1}{2}\Delta_1 h_\eta\right)\right]U_{i-1,j} +$$
$$\left[h_\eta^2\left(\gamma + \frac{1}{2}\Delta_2 h_\xi\right)\right]U_{i,j+1} + \left[h_\eta^2\left(\gamma - \frac{1}{2}\Delta_2 h_\xi\right)\right]U_{i,j-1} + \frac{1}{2}\beta h_\eta h_\xi U_{i+1,j+1} -$$
$$\frac{1}{2}\beta h_\eta h_{xi}U_{i+1,j-1} - \frac{1}{2}\beta h_\eta h_\xi U_{i-1,j+1} + \frac{1}{2}\beta h_\eta h_\xi U_{i-1,j-1} = \frac{c^2 h_\eta^2 h_\xi^2}{\mu}\frac{dp}{dz},$$

where $\alpha$, $\beta$, $\gamma$, $\Delta_1$, and $\Delta_2$ are evaluated at j). In order to solve this equation at every point, we can formulate it as a linear system of the form Au=b, where u=[$U_{1,1}$, $U_{2,1}$, ... $U_{n_e ta,1}$, $U_{1,2}$, ..., $U_{n_e ta,n_\xi}$]. We directly impose the no-slip conditions by ensuring that $$U_{i,j}=U_{n_\eta,j}=0 \text{ and } j=1,\ldots,n_\xi, \tag{55}$$

and we impose the periodic conditions with one-sided difference approximations $$\frac{U_{1,j+1} - U_{1,j}}{h_\xi} = \frac{U_{n_\xi,i+1} - U_{n_\xi,i}}{h_\xi} = 0, \text{ for } i = 1, \ldots, n_\xi, \tag{56}$$

and by ensuring $$U_{1,j}=U_{n_\xi,j}, \text{ for } i=1,\ldots,n_\xi. \tag{57}$$

The full system results in a sparse N×N matrix with nine non-zero diagonals, where N=$n_\eta n_\xi-2n_\eta-2n_\xi+4$.

5.5 Results: Velocity Profiles

After constructing the linear system described in the previous section, we solve Au=b for the velocity at the discrete points. After converting the corresponding ($\eta,\xi$) values back to Cartesian (x, y), we can plot the resulting velocity profiles. In order to display this as a continuous color map, we implement MATLAB's griddata function, which linearly interpolates the solution over a grid of the x and y values for which the equation was solved. Here we consider the effect of varying the three dimensionless parameters, namely, $\varphi$, $\theta_e$, and e, on the distribution of flow velocity in the cross-section.

5.5.1 Varying $\varphi$

Here, we consider shifting the location of the tool from the center of the channel to the edge. The parameter, $\varphi$, characterizes this offset, with $\varphi$=0 corresponding to concentric ellipses, and $\varphi$=1 representing the inner ellipse touching the circumference of the channel. Due to the definition of Bipolar coordinates, we can not set $\varphi$=0, as this would involve dividing by zero when defining $\eta_i$ and $\eta_o$. We also can't set $\varphi$=1, as this results in $\eta_1=\eta_2$, and thus we're unable to discretize the domain. Hence, to circumvent this difficulty, we approximate the largest possible shift with $\varphi$=0.01, and concentric ellipses with $\varphi$=0.99.

Figure 24:
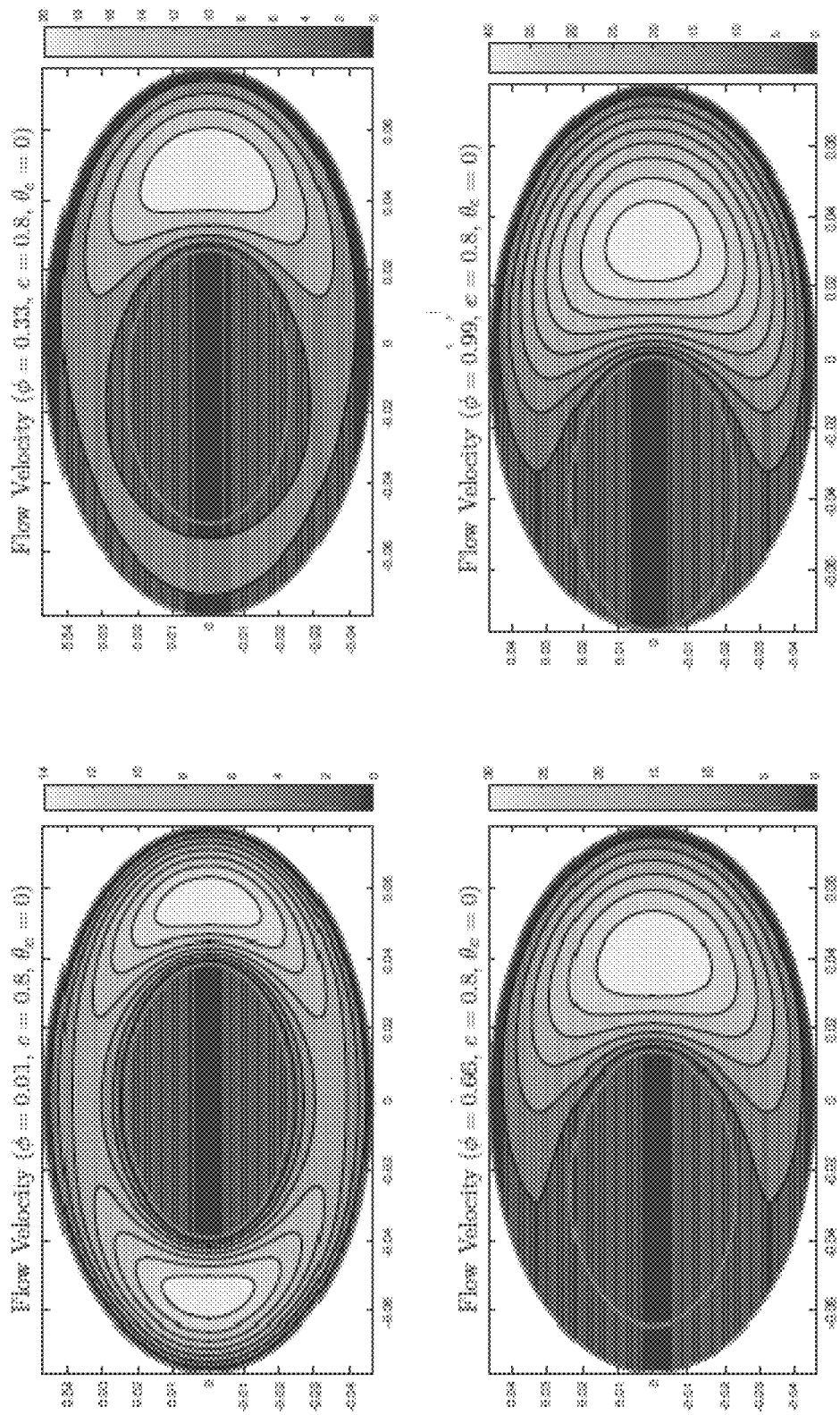
FIGS. 24-26 illustrate flow velocity profiles.

FIG. 24 illustrates flow velocity profiles for $\theta_e$=0, and e=0.8, and $\varphi$ varying from 0.01 to 0.99.

In FIG. 24, we see that as we vary $\varphi$ for a fixed eccentricity and angle of offset, that the maximum velocity achieved increases. This is intuitive, as moving the tool away from the center maximizes the maximum distance between the no-slip, or zero-velocity conditions applied to the boundaries. These velocity profiles show good agreement with COMSOL simulations, shown in A.2.

5.5.2 Varying $\theta_e$

We now fix the offset to be maximal ($\varphi=0.99$), and explore the effect of rotating the location of the tool.

Figure 25:
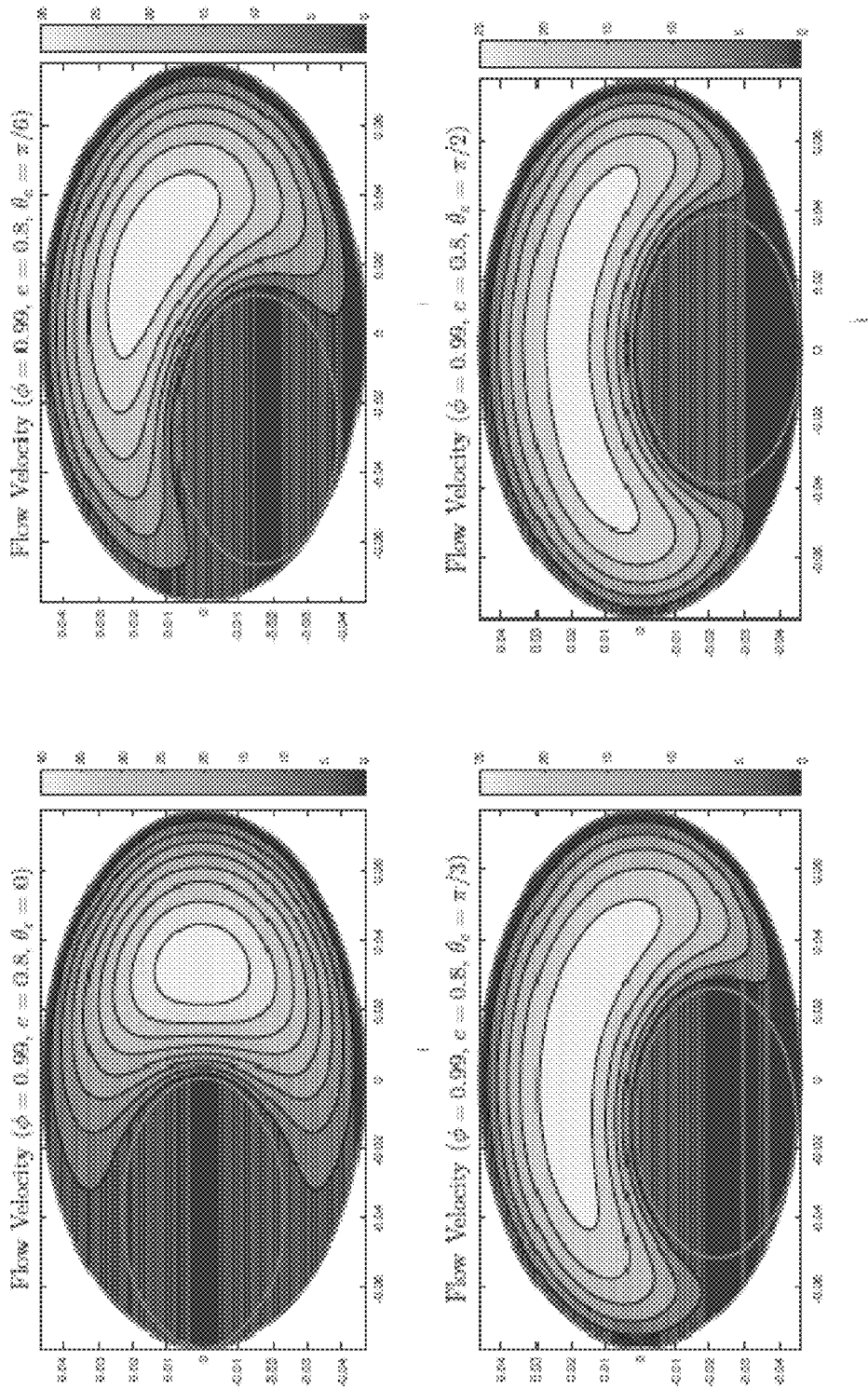

FIG. 25 illustrate flow velocity profiles for $\varphi=0.99$, $e=0.8$, and $\theta_e$ varying between 0 and $\pi/2$.

FIG. 25 shows that as we rotate the inner ellipse away from one position to another position, corresponding to increasing $\theta_e$ from 0 to $\pi/2$, that the maximum velocity decreases. As before, this corresponds with decreasing the maximum distance between the inner and outer boundaries.

5.5.3 Varying e

If we fix $\varphi=0.99$, $\theta_e=0$, and vary e, we can determine the effect of changing the eccentricity of the inner and outer ellipses.

Figure 26:
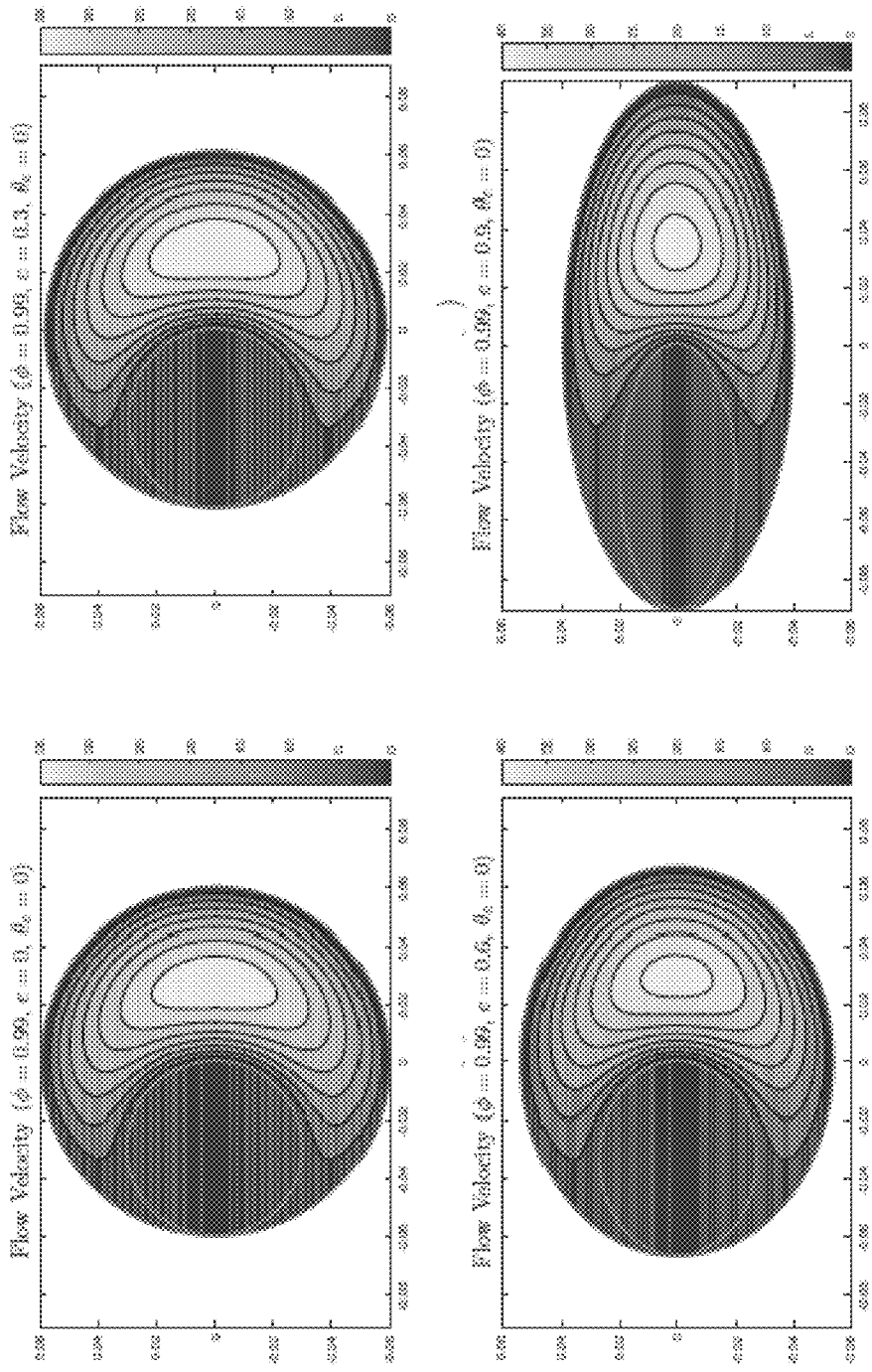

FIG. 26 illustrates flow velocity profiles for $\varphi=0.99$, $\theta_e=0$, and e varying from 0 (circular) to 0.99. Here we have constrained the cross-sectional areas of the tool and channel to be $\pi(0.03)^2$ and $\pi(0.06)^2$, respectively.

We see from FIG. 26 the effect of increasing the eccentricity, while maintaining the cross-sectional areas of the tool and channel. We see that as the eccentricity increases, the maximum velocity appears to increase as well. However, if we further increase the eccentricity, this value begins to decrease, thus suggesting that there is an optimal non-zero eccentricity value that maximizes the flow for each tool size.

5.6 Results: Volumetric Flow Rate

We can use the computed velocity profiles to calculate the volumetric flow rate, obtained by integrating the velocity over the cross-sectional domain. The volumetric flow rate is thus obtained by $$Q = \int_0^{2\pi} \int_{\eta_o}^{\eta_i} \left| \frac{\partial(x,y)}{\partial(n,\xi)} \right| u \, d\eta \, d\xi,$$

which, after explicitly calculating the Jacobian of the transformation, becomes $$Q = c^2 \sqrt{1-e^2} \int_0^{2\pi} \int_{\eta_o}^{\eta_i} \frac{u}{(\cos\xi - \cosh\eta)^2} d\eta d\xi, \quad (58)$$

We can use MATLAB's trapz which implements the Trapezoidal Rule, to approximate this integral numerically.

Figure 27:
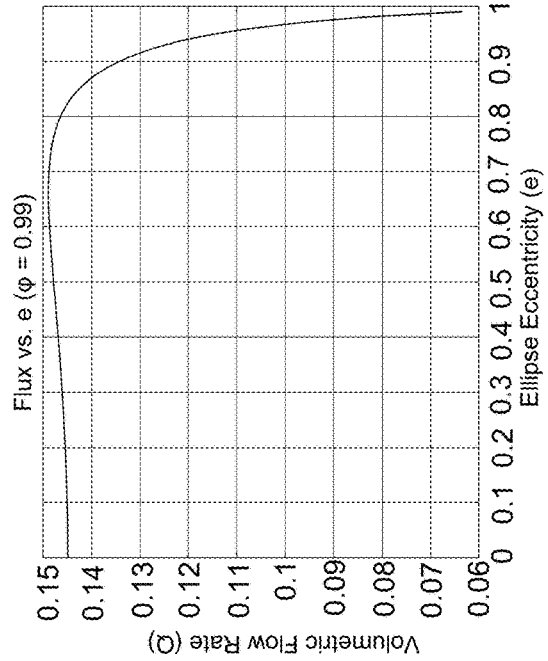
FIGS. 27 and 28 illustrate volumetric flow rate as a function of eccentricity, e, for two different values of $\varphi$.

FIGS. 27 and 28 illustrate volumetric flow rate as a function of eccentricity, e, for two different values of $\varphi$. FIG. 27 illustrates the volumetric flow rate as a function of elliptical eccentricity, for the nearly concentric case. FIG. 28 illustrates the volumetric flow rate as a function of elliptical eccentricity, for the maximally shifted inner ellipse.

In FIGS. 27 and 28 we see the effect of increasing elliptical eccentricity for two different offset values. For nearly concentric ellipses ($\varphi=0.01$), the volumetric flow rate is maximized when the ellipses have zero eccentricity, or are circular in shape. For a large offset ($\varphi=0.99$), an eccentricity value of around $e=0.7$ ensures the maximal volumetric flow rate.

Figure 29:
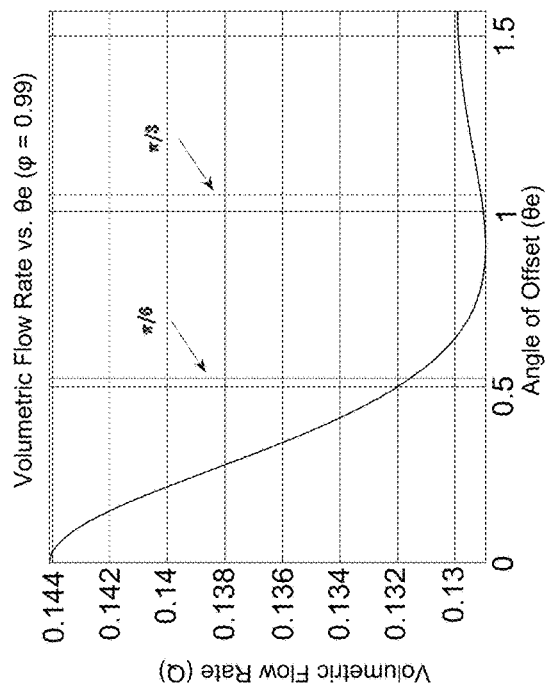
FIG. 29 is a volumetric flow rate as a function of $\theta_e$ for $\varphi=0.99$.

FIG. 29 is a volumetric flow rate as a function of $\theta_e$ for $\varphi=0.99$.

In FIG. 29, we see that the maximum volumetric flow rate is achieved when the tool is at position $\theta_e=0$. As this angle moves away from this position the flow rate rapidly decreases, but as the angle approaches $\theta_e=\pi/2$, or when the tool moves towards the bottom of the working channel, there is a small increase in flow rate.

FIGS. 30A and 30B illustrate volumetric flow rate as a function of e and $\varphi$ for $\theta_e=0$. We have calculated the volumetric flow rate at 100 points; 10 values of e and 10 values of $\varphi$. FIG. 30A illustrates the volumetric flow rate as a function of both $\varphi$ and e for $\theta_e=0$, for fixed cross-sectional areas. Tool area is $\pi(0.03)^2$ and channel area is $\varphi(0.06)^2$. FIG. 30B illustrates the volumetric flow rate as a function of both $\varphi$ and e for $\theta_e=0$, for fixed circumferences. Tool circumference is $2\pi(0.03)$ and channel circumference is $2\pi(0.06)$.

FIGS. 30A and 30B display the effect of varying both the eccentricity (e) and offset ($\varphi$) value (for a fixed angle $\theta_e=0$) on the volumetric flow rate. We see that when either the cross-sectional areas of the channel and tool (16a) or the corresponding circumferences (16b) are fixed, the maximum volumetric flow rate is achieved at maximal offset, and for a fixed non-zero eccentricity.

FIGS. 30A and 30B illustrate volumetric flow rate as a function of e and $\varphi$ for $\theta_e=0$. We have calculated the volumetric flow rate at 100 points; 10 values of e and 10 values of $\varphi$. FIG. 30A illustrates the volumetric flow rate as a function of both $\varphi$ and e for $\theta_e=0$, for fixed cross-sectional areas. Tool area is $\pi(0.03)^2$ and channel area is $\varphi(0.06)^2$. FIG. 30B illustrates the volumetric flow rate as a function of both $\varphi$ and e for $\theta_e=0$, for fixed circumferences. Tool circumference is $2\pi(0.03)$ and channel circumference is $2\pi(0.06)$.

FIG. 31 illustrates the maximum eccentricity value predicted for $\varphi=0.99$ and $\theta_e=0$, as the cross-sectional area of the tool increases. This was calculated over 10000 points; 100 eccentricity values, and 100 cross-sectional areas.

In FIG. 31 we see the evolution of the optimal eccentricity value for increasing tool size. From this, we see that as the size of the tool tends to zero, the optimal eccentricity approaches zero as well. This is to be expected, as the maximal flow rate in an unobstructed channel is attained for a circular geometry. As the size of the tool increases, the tool and channel must be more eccentric to maximize the flow rate.

The following references are hereby incorporated by reference (1) K. F. Riley, M. P. Hobson, and S. J. Bence. *Mathematical Methods for Physics and Engineering*. Cambridge University Press, Cambridge, United Kingdom, 2006; and (2) William T. Snyder and Gerald A. Goldstein. An analysis of fully developed laminar flow in an eccentric annulus. *AIChE Journal*, 11(3):462-467, 1965.

A Validation of Velocity Profiles

A.1 Circular Domains: Analytical Solution

Figure 32:
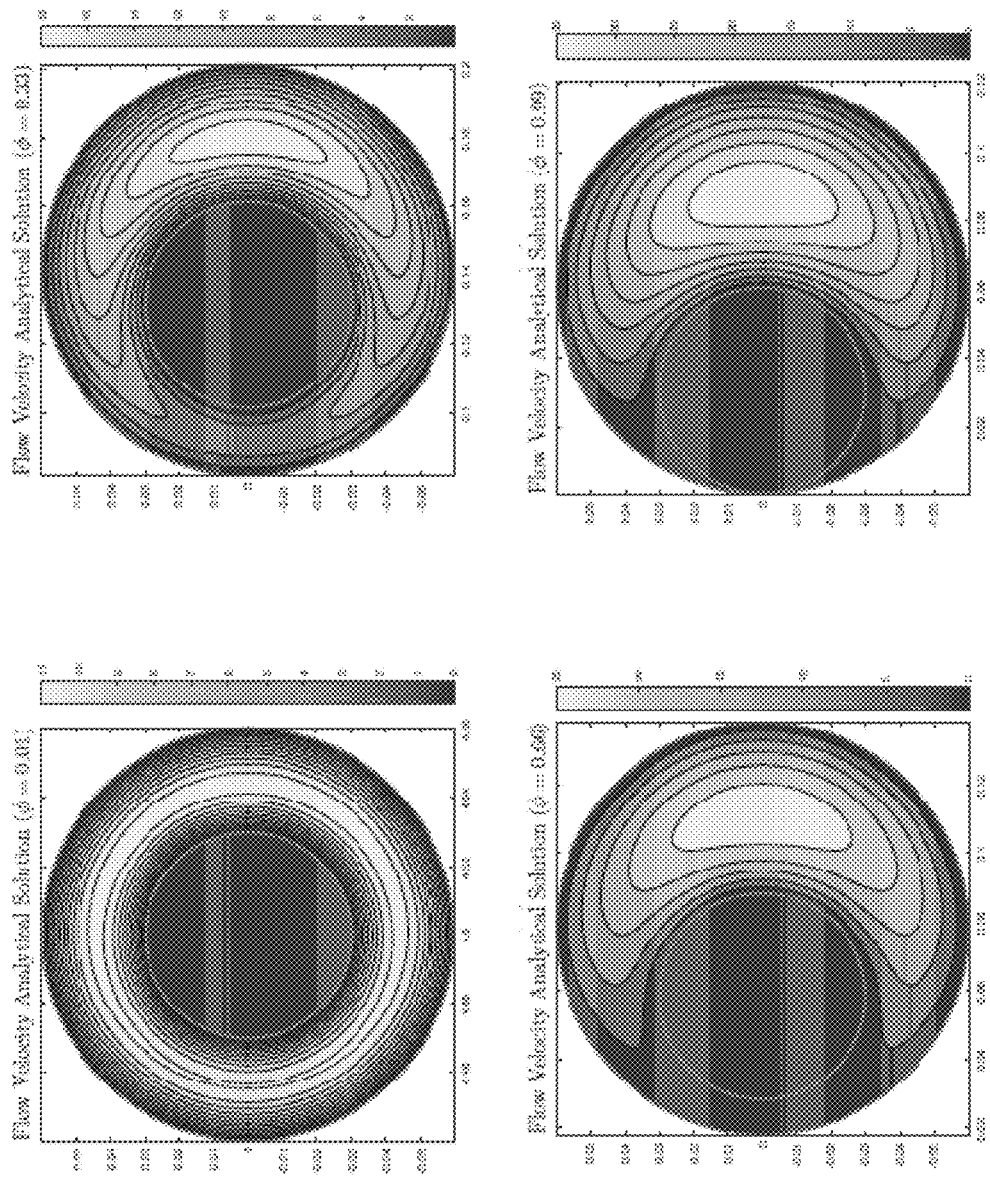
FIG. 32 illustrates flow velocity profiles for $r_1=0.03$, $r_2=0.06$, and $\varphi$ varying from 0.01 to 0.99.

FIG. 32 illustrates flow velocity profiles for $r_1=0.03$, $r_2=0.06$, and $\varphi$ varying from 0.01 to 0.99. We have shifted the domain so the outer circle is centered at (0, 0). These are obtained from the analytical solution (39) with a fifty-term approximation to the infinite sum.

A.2 Elliptical Domains: COMSOL Simulations

Figure 33:
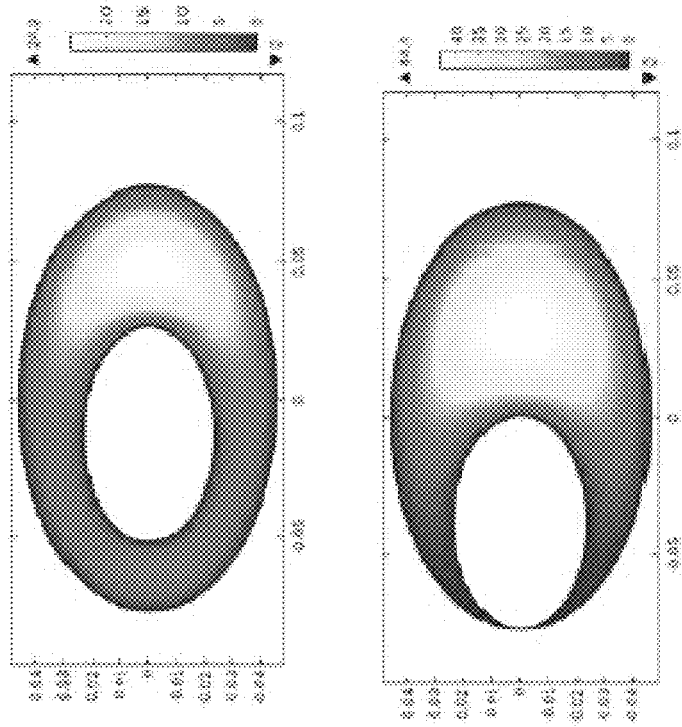
FIG. 33 illustrates elliptical velocity profiles for $e=0.8$, $\theta_e=0$, and $\varphi$ varying from 0.01 to 0.99.
Figure 33:
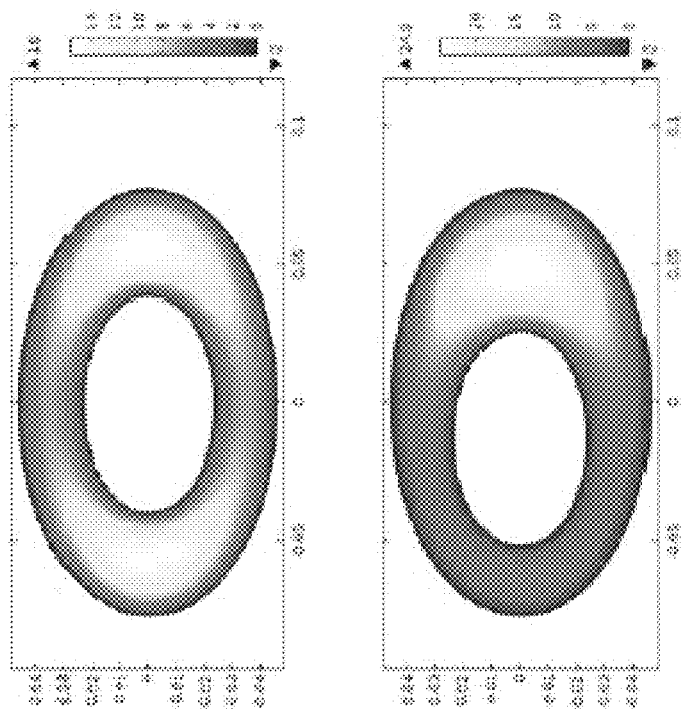

FIG. 33 illustrates elliptical velocity profiles for $e=0.8$, $\theta_e=0$, and $\varphi$ varying from 0.01 to 0.99. The areas are constrained to be that of a circular tool and channel with radii 0.03 and 0.06, respectively. These are generated by solving the governing equation (6) in the required domain on COMSOL.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
an elongate member having a first end portion and a second end portion defining a longitudinal axis, the elongate member including a sidewall, the sidewall includes an inner surface and an outer surface disposed opposite the inner surface, the inner surface defining a lumen, the lumen having a non-circular cross-sectional shape, the lumen has a first diameter of a size between 0.30 cm and 0.40 cm, the lumen has a second diameter of a size between 0.35 cm and 0.45 cm;
a positioning member being disposed on the inner surface of the sidewall that extends parallel to the longitudinal axis of the elongate member from the first end portion to the second end portion, the positioning member being configured to retain a medical instrument within one side portion of the lumen such that the medical instrument extends along a longitudinal axis, the longitudinal axis of the medical instrument being offset from the longitudinal axis of the elongate member;
a side port defining a lumen, the lumen of the side port being in fluid communication with the lumen defined by the sidewall, the side port including a valve disposed within the lumen defined by the side port, the valve being configured to regulate flow of material within the lumen defined by the side port; and
a collection member coupled to the side port, the collection member including a filter and being configured to collect material that passes through the lumen defined by the side port.

2. The medical device of claim 1, wherein the first diameter is disposed substantially perpendicular to the second diameter.

3. The medical device of claim 1, wherein the positioning member includes a first positioning member and a second positioning member, the first positioning member being disposed within the lumen defined by the sidewall, the second positioning member being disposed within the lumen, the second positioning member being spaced from and disposed distally of the first positioning member.

4. The medical device of claim 1, wherein the positioning member includes a first positioning member and a second positioning member, the first positioning member being disposed within the lumen defined by the sidewall, the second positioning member being disposed within the lumen, the second positioning member being spaced from and disposed adjacent the first positioning member.

5. The medical device of claim 1, further comprising:
a handle member coupled to the elongate member.

6. The medical device of claim 1, wherein the side port is disposed at a non-perpendicular angle with respect to the longitudinal axis of the elongate member.

7. The medical device of claim 1, wherein
the side port includes a valve disposed within the lumen defined by the side port, the valve being configured to regulate flow of material within the lumen defined by the side port,
the valve being disposed between the elongate member and the collection member.

8. A medical device, comprising:
an elongate member having a first end portion and a second end portion defining a longitudinal axis, the elongate member including a sidewall, the sidewall including an inner surface and an outer surface opposite the inner surface, the inner surface defines a lumen, the lumen having a non-circular cross-sectional shape, the elongate member including a first positioning member, a second positioning member, and a third positioning member disposed on the inner surface of the sidewall, the third positioning member being disposed between the first positioning member and the second positioning member, the first positioning member, the second positioning member and the third positioning member being configured to help retain a medical instrument within one side portion of the lumen such that the medical instrument extends along a longitudinal axis, the longitudinal axis of the medical instrument being offset from the longitudinal axis of the elongate member;
a side port defining a lumen, the lumen of the side port being in fluid communication with the lumen defined by the sidewall, the side port including a valve disposed within the lumen defined by the side port, the valve being configured to regulate flow of material within the lumen defined by the side port; and
a collection member coupled to the side port, the collection member including a filter and being configured to collect material that passes through the lumen defined by the side port.

9. The medical device of claim 8, further comprising:
a handle member coupled to the elongate member.

10. The medical device of claim 8, wherein the valve is a stop cock type valve.

11. A method of using a medical device, comprising:
inserting the medical device into a body of a patient, the medical device including an elongate member having a first end portion and a second end portion defining a longitudinal axis, the elongate member including a sidewall, the sidewall including an inner surface and an outer surface opposite the inner surface, the inner surface defines a lumen, the lumen having a non-circular cross-sectional shape, the lumen has a first diameter of a first size and a second diameter of a second size, the first size being about 0.3 mm larger than the second size, the elongate member including a positioning member disposed on the inner surface of the sidewall that extends parallel to the longitudinal axis of the elongate member from the first end portion to the second end portion, the medical device including a side port defining a lumen, the lumen of the side port being in fluid communication with the lumen defined by the sidewall, the side port including a valve disposed within the lumen defined by the side port, the valve being configured to regulate flow of material within the lumen defined by the side port, and a collection member coupled to the side port, the collection member including a filter; and
inserting a medical instrument into the lumen disposed on one side portion of the lumen such that the medical instrument extends along a longitudinal axis, the longitudinal axis of the medical instrument being offset from the longitudinal axis of the elongate member.

12. The method of claim 11, further comprising:
collecting material that passes through the lumen defined by the side port.

* * * * *